US011004197B2

(12) United States Patent
Kashima et al.

(10) Patent No.: US 11,004,197 B2
(45) Date of Patent: May 11, 2021

(54) MEDICAL IMAGE PROCESSING APPARATUS, MEDICAL IMAGE PROCESSING METHOD, AND PROGRAM

(71) Applicant: Sony Corporation, Tokyo (JP)

(72) Inventors: Koji Kashima, Kanagawa (JP); Takami Mizukura, Kanagawa (JP); Kazunori Kamio, Kanagawa (JP); Yiwen Zhu, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 37 days.

(21) Appl. No.: 16/469,152

(22) PCT Filed: Dec. 14, 2017

(86) PCT No.: PCT/JP2017/044860
§ 371 (c)(1),
(2) Date: Jun. 13, 2019

(87) PCT Pub. No.: WO2018/123613
PCT Pub. Date: Jul. 5, 2018

(65) Prior Publication Data
US 2020/0098104 A1 Mar. 26, 2020

(30) Foreign Application Priority Data

Dec. 28, 2016 (JP) .............................. JP2016-256731

(51) Int. Cl.
*G06K 9/00* (2006.01)
*G06T 7/00* (2017.01)
(Continued)

(52) U.S. Cl.
CPC ........ *G06T 7/0012* (2013.01); *A61B 1/00004* (2013.01); *A61B 1/06* (2013.01);
(Continued)

(58) Field of Classification Search
CPC . A61B 1/00004; A61B 1/00009; A61B 1/043; A61B 1/06; G02B 23/24;
(Continued)

(56) References Cited

U.S. PATENT DOCUMENTS

| 2010/0195904 A1* | 8/2010 | Tsuruoka ................. A61B 1/05 |
| | | 382/165 |
| 2011/0239056 A1* | 9/2011 | Adams .................. G06F 11/328 |
| | | 714/48 |
| 2017/0367580 A1* | 12/2017 | DiMaio .................. A61B 5/445 |

FOREIGN PATENT DOCUMENTS

| JP | 2007-313171 A | 12/2007 |
| JP | 2011-87906 A | 5/2011 |

(Continued)

OTHER PUBLICATIONS

International Search Report and Written Opinion dated Jan. 30, 2018 for PCT/JP2017/044860 filed on Dec. 14, 2017, 9 pages including English Translation of the International Search Report.

*Primary Examiner* — Xin Jia
(74) *Attorney, Agent, or Firm* — Xsensus LLP

(57) ABSTRACT

A coefficient calculator calculates a correlation coefficient representing a correlation between a normal frame, which is imaged in a state in which normal light is applied to a subject, and a special frame, which is imaged in a state in which special light is applied to the subject; and a processing unit that applies image processing to the special frame so that a part in which the correlation coefficient is high and a part in which the correlation coefficient is low are displayed differently in the special frame. Further provided are: a first determination unit that calculates, for each pixel or each area of the normal frame, a first determination value representing a probability that a predetermined site is imaged; and a second determination unit that calculates, for each pixel or each area of the special frame, a second determination value
(Continued)

representing a probability that a predetermined site is imaged.

13 Claims, 13 Drawing Sheets

(51) Int. Cl.
*A61B 1/00* (2006.01)
*A61B 1/06* (2006.01)

(52) U.S. Cl.
CPC ............... *G06T 2207/30096* (2013.01); *G06T 2207/30101* (2013.01)

(58) Field of Classification Search
CPC . G06T 2207/30096; G06T 2207/30101; G06T 7/0012; H04N 7/18
See application file for complete search history.

(56) References Cited

FOREIGN PATENT DOCUMENTS

| | | | |
|---|---|---|---|
| JP | 2011-98088 | A | 5/2011 |
| JP | 2011-167337 | A | 9/2011 |
| JP | 2012-24283 | A | 2/2012 |
| JP | P5320268 | B2 | 10/2013 |
| JP | 2016-93210 | A | 5/2016 |
| WO | 2015/025640 | A1 | 2/2015 |

* cited by examiner

MEDICAL IMAGE PROCESSING APPARATUS, MEDICAL IMAGE PROCESSING METHOD, AND PROGRAM

CROSS-REFERENCE TO RELATED APPLICATIONS

The present application is based on PCT filing PCT/JP2017/044860, filed Dec. 14, 2017 which claims priority to JP 2016-256731, filed Dec. 28, 2016, the entire contents of each are incorporated herein by reference.

TECHNICAL FIELD

The present technique relates to a medical image processing apparatus, a medical image processing method, and a program, and, for example, relates to a medical image processing apparatus, a medical image processing method, and a program that can combine and display a normal image, which is captured by applying normal light such as white light to a human body, and a special image, which is captured by applying special light to indicate a position of a blood vessel.

BACKGROUND ART

In the past, for example, various techniques for use in medical settings have been proposed, in which a normal image of an organ or the like captured by an endoscope apparatus is combined with a special image indicating a position of a lesion, such as a blood vessel and a tumor, that is hard to distinguish in the normal image.

For example, capturing the normal image and the special image in time division is described in PTL 1. In addition, for example, combining and displaying the normal image and the special image is described in PTL 2. In addition, combining and displaying the normal image and the special image and flashing the special image is described in PTL 3.

Here, the normal image denotes an image captured by applying normal light, such as white light, to an organ or the like as a subject. The special light denotes an image captured by applying special light with a predetermined wavelength different from the normal light. Note that in capturing the special image, a fluorescent agent or the like that reacts to the application of the special light may be mixed or applied to a blood vessel (blood) or a lesion as a subject.

CITATION LIST

Patent Literature

[PTL 1]
JP 2007-313171A
[PTL 2]
JP 2012-24283A
[PTL 3]
Japanese Patent No. 5320268

SUMMARY

Technical Problem

A blood vessel and the like not captured in the normal image are also captured in the special image, and it is desirable that different parts in the special image and the normal image can be recognized at a glance in an image obtained by combining the special image and the normal image.

The present technique has been made in view of the circumstances, and the present technique can combine a normal image and a special image such that different parts can be recognized.

Solution to Problem

An aspect of the present technique provides a medical image processing apparatus including: a coefficient calculation unit that calculates a correlation coefficient representing a correlation between a normal frame, which is imaged in a state in which normal light is applied to a subject, and a special frame, which is imaged is a state in which special light is applied to the subject; and a processing unit that applies image processing to the special frame so that a part in which the correlation coefficient is high and a part in which the correlation coefficient is low are displayed differently in the special frame.

An aspect of the present technique provides a medical image processing method including the steps of: calculating a correlation coefficient representing a correlation between a normal frame, which is imaged in a state in which normal light is applied to a subject, and a special frame, which is imaged in a state in which special light is applied to the subject; and applying image processing to the special frame so that a part in which the correlation coefficient is high and a part in which the correlation coefficient is low are displayed differently in the special frame.

An aspect of the present technique provides a program for causing a computer to execute a process including the steps of: calculating a correlation coefficient representing a correlation between a normal frame, which is imaged in a state in which normal light is applied to a subject, and a special frame, which is imaged in a state in which special light is applied to the subject; and applying image processing to the special frame so that a part in which the correlation coefficient is high and a part in which the correlation coefficient is low are displayed differently in the special frame.

In the medical image processing apparatus, the medical image processing method, and the program according to the aspects of the present technique, the correlation coefficient is calculated. The correlation coefficient represents the correlation between the normal frame, which is imaged in the state in which the normal light is applied to the subject, and the special frame, which is imaged in the state in which the special light is applied to the subject. The image processing is applied to the special frame so that the part in which the correlation coefficient is high and the part in which the correlation coefficient is low are displayed differently in the special frame.

Note that the medical image processing apparatus may be an independent apparatus or may be an internal block included in one apparatus.

In addition, the program can be provided by transmitting the program through a transmission medium or can be provided by recording the program in a recording medium.

Advantageous Effect of Invention

According to the aspects of the present technique, a normal image and a special image can be combined such that different parts can be recognized.

Note that the advantageous effect described here may not be limited, and the advantageous effect may be any of the advantageous effects described in the present disclosure.

DESCRIPTION OF EMBODIMENT

Hereinafter, a mode for carrying out the present technique (hereinafter, referred to as embodiment) will be described.
<Configuration of Endoscope System>

The technique according to the present disclosure can be applied to various products. For example, the technique according to the present disclosure may be applied to an endoscopic surgery system. In addition, although an example of the endoscopic surgery system will be described here, the present technique can also be applied to a surgical operation system, a microsurgery system, and the like.

Figure 1:
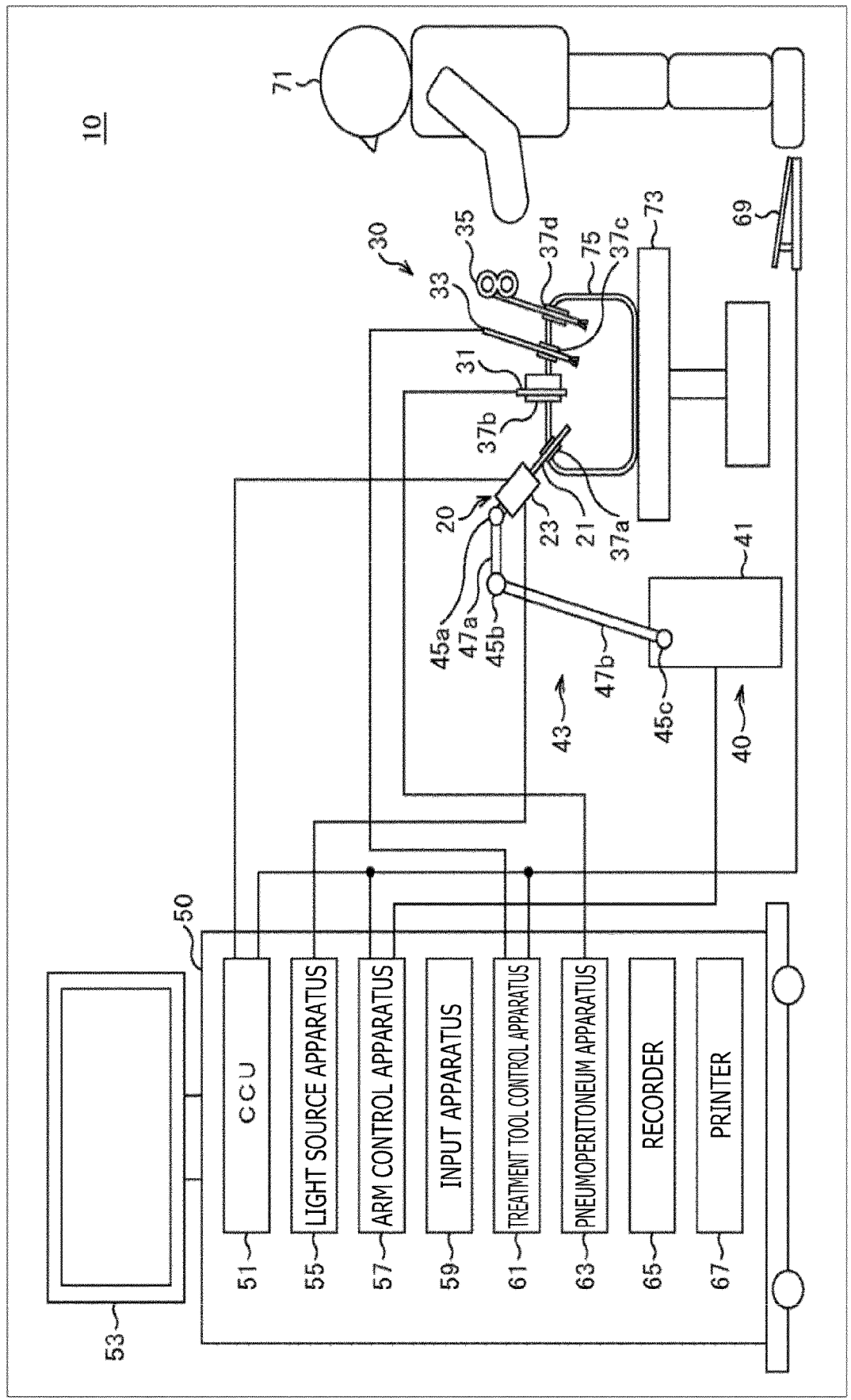
FIG. 1 is a diagram illustrating a configuration of an embodiment of an endoscopic surgery system according to the present technique.

FIG. 1 is a diagram illustrating an example of a schematic configuration of an endoscopic surgery system 10 to which the technique according to the present disclosure can be applied. FIG. 1 illustrates a situation in which a surgeon (doctor) 71 uses the endoscopic surgery system 10 to perform a surgery of a patient 75 on a patient bed 73. As illustrated in FIG. 1, the endoscopic surgery system 10 includes an endoscope 20, other surgical tools 30, a support arm apparatus 40 that supports the endoscope 20, and a cart 50 provided with various apparatuses for endoscopic surgery.

In the endoscopic surgery, instead of performing a laparotomy involving incision of the abdominal wall, the abdominal wall is punctured by a plurality of cylindrical opening devices called trocars 37a to 37d. Furthermore, a barrel 21 of the endoscope 20 and the other surgical tools 30 are inserted into a body cavity of the patient 75 from the trocars 37a to 37d. In the illustrated example, the other surgical tools 30 inserted into the body cavity of the patient 75 include a pneumoperitoneum tube 31, an energy treatment tool 33, and a forceps 35. Furthermore, the energy treatment tool 33 is a treatment tool that uses high-frequency current or ultrasonic vibration to perform operation, such as incising and separating tissue and sealing a blood vessel. However, the illustrated surgical tools 30 are just an example, and various surgical tools generally used in the endoscopic surgery, such as tweezers and retractors, may be used as the surgical tools 30.

An image of the surgical site in the body cavity of the patient 75 photographed by the endoscope 20 is displayed on a display apparatus 53. The surgeon 71 uses the energy treatment tools 33 and the forceps 35 while viewing in real time the image of the surgical site displayed on the display apparatus 53 to perform treatment, such as excising the affected part. Note that the pneumoperitoneum tube 31, the energy treatment tools 33, and the forceps 35 are supported by the surgeon 71, an assistant, or the like during the surgery.
(Support Arm Apparatus)

The support arm apparatus 40 includes an arm portion 43 extending from a base portion 41. In the illustrated example, the arm portion 43 includes joint portions 45a, 45b, and 45c and links 47a and 47b, and an arm control apparatus 57 controls and drives the arm portion 43. The arm portion 43 supports the endoscope 20 and controls the position and the posture of the endoscope 20. This can realize stable fixation of the position of the endoscope 20.
(Endoscope)

The endoscope 20 includes the barrel 21 in which an area of a predetermined length from the tip is inserted into the body cavity of the patient 75, and a camera head 23 connected to the base end of the barrel 21. Although the endoscope 20 is a so-called rigid scope including a rigid barrel 21 in the illustrated example, the endoscope 20 may be a so-called flexible scope including a flexible barrel 21.

An opening portion for inserting an object lens is provided at the tip of the barrel 21. A light source apparatus 55 is connected to the endoscope 20, and a light guide extended inside of the barrel 21 guides light generated by the light source apparatus 55 to the tip of the barrel. The light is applied toward an observation target in the body cavity of the patient 75 through the objective lens. Note that the endoscope 20 may be a forward-viewing endoscope or may be an oblique-viewing endoscope or a side-viewing endoscope.

An optical system and an imaging device are provided inside of the camera head 23, and the optical system condenses reflected light (observation light) from the observation target on the imaging device. The imaging device photoelectrically converts the observation light, and an electrical signal corresponding to the observation light, that is, an image signal corresponding to the observation image, is generated. The image signal is transmitted as raw data to a camera control unit (CCU) 51. Note that the camera head 23 has a function of appropriately driving the optical system to adjust the magnification and the focal length.

Note that a plurality of imaging devices may be provided on the camera head 23 to correspond to, for example, stereoscopic view (3D display). In this case, a plurality of relay optical systems are provided inside of the barrel 21 to guide the observation light to each of the plurality of imaging devices.
(Various Apparatuses Mounted on Cart)

The CCU 51 includes a CPU (Central Processing Unit), a CPU (Graphics Processing Unit), and the like and comprehensively controls the operation of the endoscope 20 and the display apparatus 53. Specifically, the CCU 51 applies various types of image processing, such as a development process (demosaic processing), to the image signal received from the camera head 23 in order to display an image based on the image signal. The CCU 51 provides the image signal after the image processing to the display apparatus 53. The CCU 51 also transmits control signal to the camera head 23 and controls the drive of the camera head 23. The control signal may include information regarding imaging conditions, such as magnification and focal length.

The display apparatus 53 is controlled by the CCU 51 to display an image based on the image signal after the image processing by the CCU 51. In a case where the endoscope 20 corresponds to, for example, high-resolution imaging, such as 4K (3840 horizontal pixels×2160 vertical pixels) or 8K (7680 horizontal pixels×4320 vertical pixels), and/or in a case where the endoscope 20 corresponds to 3D display, the display apparatus 53 that can perform high-resolution display and/or 3D display can be used according to the cases. In the case where the endoscope 20 corresponds to high-resolution imaging, such as 4K and 8K, the display apparatus 53 in a size of 55 inches or more can be used to obtain a higher sense of immersion. In addition, a plurality of display apparatuses 53 with different resolutions and sizes may be provided according to the use.

The light source apparatus 55 includes a light source, such as an LED (light emitting diode), and supplies illumination light for imaging the surgical site to the endoscope 20.

The arm control apparatus 57 includes a processor, such as a CPU, and operates according to a predetermined program to control the drive of the arm portion 43 of the support arm apparatus 40 according to a predetermined control system.

An input apparatus 59 is an input interface for the endoscopic surgery system 10. The user can input various types of information or instructions to the endoscopic surgery system 10 through the input apparatus 59. For example, the user inputs various types of information regarding the surgery, such as biological information of patient and information regarding procedure of surgery, through the input apparatus 59. The user also inputs, for example, an instruction for driving the arm portion 43, an instruction for changing the imaging conditions of the endoscope 20 (such as type of illumination light, magnification, and focal length), an instruction for driving the energy treatment tool 33, and the like through the input apparatus 59.

The type of input apparatus 59 is not limited, and the input apparatus 59 may be various well-known input apparatuses. The input apparatus 59 can be, for example, a mouse, a keyboard, a touch panel, a switch, a foot switch 69, and/or a lever. In the case where the touch panel is used as the input apparatus 59, the touch panel may be provided on the display surface of the display apparatus 53.

Alternatively, the input apparatus 59 is a device worn by the user, such as an eyeglass-type wearable device and an HMD (Head Mounted Display), and various inputs are performed according to gestures or glances of the user detected by the devices. The input apparatus 59 also includes a camera that can detect the motion of the user, and various inputs are performed according to gestures or glances of the user detected from the video imaged by the camera.

The input apparatus 59 further includes a microphone that can collect the voice of the user, and various inputs are performed according to the sound through the microphone. In this way, the input apparatus 59 allows non-contact input of various types of information, and this particularly allows a user (for example, surgeon 71) belonging to a clean area to perform non-contact operation of the device belonging to an unclean area. In addition, the user can operate the device without releasing the possessed surgical tool, and this improves the convenience of the user.

A treatment tool control apparatus 61 controls the drive of the energy treatment tool 33 for cauterizing the tissue, incising the tissue, or sealing the blood vessel. A pneumoperitoneum apparatus 63 feeds a gas into the body cavity of the patient 75 through the pneumoperitoneum tube 31 to inflate the body cavity in order to secure the visual field of the endoscope 20 and secure the workspace of the surgeon. A recorder 65 is an apparatus that can record various types of information regarding the surgery. A printer 67 is an apparatus that can print various types of information regarding the surgery in various formats, such as text, image, and graph.

Hereinafter, particularly characteristic components in the endoscopic surgery system 10 will be described in more detail.

(Support Arm Apparatus)

The support arm apparatus 40 includes the base portion 41 as a base and the arm portion 43 extending from the base portion 41. Although the arm portion 43 includes the plurality of joint portions 45a, 45b, and 45c and the plurality of links 47a and 47b connected by the joint portion 45b in the illustrated example, the configuration of the arm portion 43 is simply illustrated in FIG. 1 for the simplification.

Actually, the shapes, the numbers, and the arrangement of the joint portions 45a to 45c and the links 47a and 47b, the directions of the axes of rotation of the joint portions 45a to 45c, and the like can be appropriately set so that the arm portion 43 has a desirable degree of freedom. For example, the arm portion 43 can be suitably configured to have a degree of freedom equal to or greater than six degrees of freedom. As a result, the endoscope 20 can be freely moved within the removable range of the arm portion 43, and the barrel 21 of the endoscope 20 can be inserted into the body cavity of the patient 75 from a desirable direction.

Actuators are provided for the joint portions 45a to 45c, and the joint portions 45a to 45c can be driven by the actuators to rotate about predetermined axes of rotation. The arm control apparatus 57 controls the drive of the actuators to control the rotation angle of each of the joint portions 45a to 45c to control the drive of the arm portion 43. This can realize control of the position and the posture of the endoscope 20. In this case, the arm control apparatus 57 can use various well-known control systems, such as force control and position control, to control the drive of the arm portion 43.

For example, the surgeon 71 may appropriately input an operation through the input apparatus 59 (including foot switch 69), and the arm control apparatus 57 may appropriately control the drive of the arm portion 43 according to the input of the operation to control the position and the posture of the endoscope 20. The control can move the endoscope 20 at the tip of the arm portion 43 from an arbitrary position to an arbitrary position, and the endoscope 20 can be fixed and supported at the position after the movement. Note that the arm portion 43 may be operated by a so-called master-slave system. In this case, the user can remotely control the arm portion 43 through the input apparatus 59 installed at a place away from the operating room.

Furthermore, in the case where the force control is applied, the arm control apparatus 57 may perform so-called power assist control for receiving external force from the user to drive the actuators of the joint portions 45a to 45c to smoothly move the arm portion 43 according to the external force. This allows the user to move the arm portion 43 with relatively small force when the user directly touches the arm portion 43 to move the arm portion 43. Therefore, the endoscope 20 can be more intuitively moved with a simpler operation, and the convenience of the user can be improved.

Here, a doctor called an endoscopist generally supports the endoscope 20 in the endoscopic surgery. On the other hand, the support arm apparatus 40 can be used to more reliably fix the position of the endoscope 20 without manpower. This enables stable acquisition of images of the surgical site, and the surgery can be smooth.

Note that the arm control apparatus 57 may not be provided on the cart 50. In addition, the arm control apparatus 57 may not be one apparatus. For example, the arm control apparatus 57 may be provided on each of the joint portions 45a to 45c of the arm portion 43 of the support arm apparatus 40, and the plurality of arm control apparatuses 57 may work together to realize the drive and control of the arm portion 43.

(Light Source Apparatus)

The light source apparatus 55 supplies illumination light for imaging the surgical site to the endoscope 20. The light source apparatus 55 includes a white light source including, for example, an LED, a laser light source, or a combination of these. In this case, in a case where the white light source includes a combination of RGB laser light sources, the output intensity and the output timing of each color (each wavelength) can be highly accurately controlled. Therefore, the light source apparatus 55 can adjust the white balance of the captured image.

Furthermore, in this case, the laser light from each of the RGB laser light sources can be applied to the observation target in time division, and the drive of the imaging device of the camera head 23 can be controlled in synchronization with the application timing. Therefore, images corresponding to RGB can also be taken in time division. According to the method, a color image can be obtained without providing a color filter in the imaging device.

In addition, the drive of the light source apparatus 55 may be controlled to change the intensity of output light at each predetermined time period. The drive of the imaging device of the camera head 23 can be controlled in synchronization with the timing of change in the intensity of light, and images can be acquired in time division and combined. This can generate an image with a high dynamic range without so-called blocked-up shadows or blown-out highlights.

The light source apparatus 55 may also be able to supply light at a predetermined wavelength band corresponding to special light imaging. In the special light imaging, so-called narrow band imaging is performed in which, for example, the wavelength dependence of the absorption of light in the body tissue is used to apply light in a narrower band than the illumination light (that is, white light) during normal observation to thereby image predetermined tissue, such as a blood vessel of mucosal surface layer, at high contrast.

Alternatively, fluorescence imaging for using fluorescence generated by applying excitation light to obtain an image may be performed in the special light imaging. In the fluorescence imaging, excitation light may be applied to the body tissue to observe fluorescence from the body tissue (autofluorescence imaging), or a fluorescence image may be obtained by locally injecting a reagent, such as indocyanine green (ICC), 5-ALA (5-aminolevulinic acid), and Laserphyrin, into body tissue and applying excitation light corresponding to the fluorescence wavelength of the reagent to the body tissue. The light source apparatus 55 can supply the narrow-band light and/or the excitation light corresponding to the special light imaging.

(Camera Head and CCU)

Figure 2:
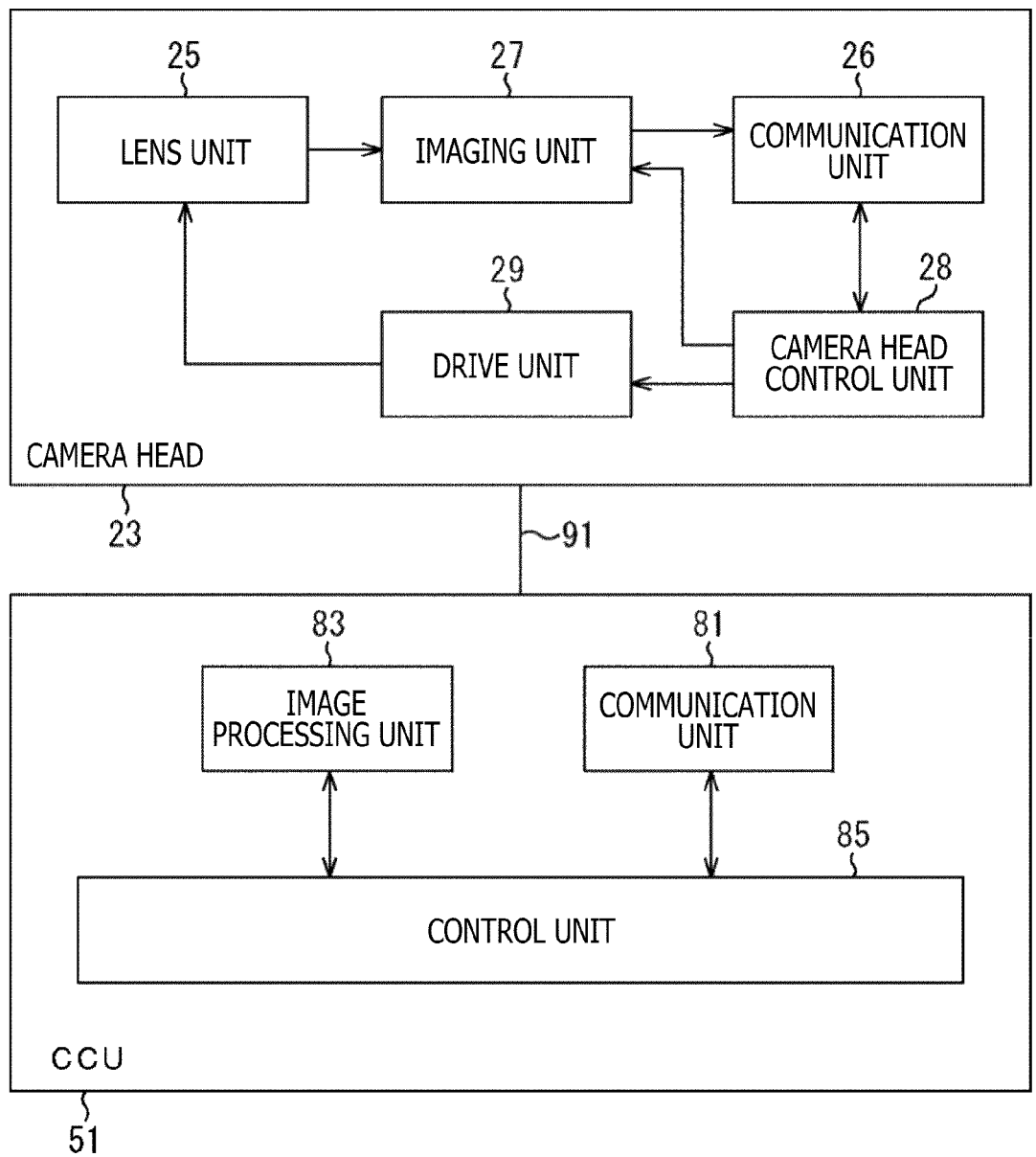
FIG. 2 is a block diagram illustrating an example of a functional configuration of a camera head and a CCU.

The functions of the camera head 23 of the endoscope 20 and the CCU 51 will be described in more detail with reference to FIG. 2. FIG. 2 is a block diagram illustrating an example of a functional configuration of the camera head 23 and the CCU 51 illustrated in FIG. 1.

With reference to FIG. 2, the camera head 23 has functions including a lens unit 25, an imaging unit 27, a drive unit 29, a communication unit 26, and a camera head control unit 28. Furthermore, the CCU 51 has functions including a communication unit 81, an image processing unit 83, and a control unit 85. The camera head 23 and the CCU 51 are connected and can communicate in both directions through a transmission cable 91.

First, the functional configuration of the camera head 23 will be described. The lens unit 25 is an optical system provided at a connection between the camera head 23 and the barrel 21. Observation light introduced from the tip of the barrel 21 is guided to the camera head 23 and enters the lens unit 25. The lens unit 25 includes a combination of a plurality of lenses including a zoom lens and a focus lens. The optical characteristics of the lens unit 25 are adjusted to condense the observation light on the light receiving surface of an imaging device of the imaging unit 27. In addition, the positions of the zoom lens and the focus lens on the optical axis can be moved to adjust the magnification and the focus of the captured image.

The imaging unit 27 includes the imaging device and is arranged in a later stage of the lens unit 25. The observation light passing through the lens unit 25 is condensed on the light receiving surface of the imaging device, and an image signal corresponding to the observation image is generated by photoelectric conversion. The image signal generated by the imaging unit 27 is provided to the communication unit 26.

The imaging device included in the imaging unit 27 is, for example, a CMOS (Complementary Metal Oxide Semiconductor) type image sensor and is capable of color imaging with a Bayer array. Note that an example of the imaging device that can be used includes an imaging device that can correspond to photographing of an image at high resolution of 4K or more. The surgeon 71 can figure out the situation of the surgical site in more detail by obtaining a high-resolution image of the surgical site, and the surgery can be more smoothly advanced.

In addition, the imaging device of the imaging unit 27 includes a pair of imaging devices for acquiring an image signal for right eye and an image signal for left eye corresponding to 3D display. The 3D display allows the surgeon 71 to more accurately figure out the depth of the living body tissue at the surgical site. Note that in a case where the imaging unit 27 is a multiple disc type, a plurality of systems of lens units 25 are also provided according to the imaging devices.

In addition, the imaging unit 27 may not be provided on the camera head 23. For example, the imaging unit 27 may be provided immediately after the objective lens inside of the barrel 21.

The drive unit 29 includes an actuator, and the camera head control unit 28 controls the actuator to move the zoom lens and the focus lens of the lens unit 25 by a predetermined distance along the optical axis. As a result, the magnification and the focus of the image captured by the imaging unit 27 can be appropriately adjusted.

The communication unit 26 includes a communication apparatus that transmits and receives various types of information to and from the CCU 51. The communication unit 26 transmits raw data of an image signal obtained from the imaging unit 27 to the CCU 51 through the transmission cable 91. In this case, it is preferable to transmit the image signal through optical communication to display the captured image of the surgical site at low latency.

This is because in the surgery, the surgeon 71 uses the captured image to observe the state of the affected part and performs the surgery. Therefore, moving images of the surgical site need to be displayed in real time as much as possible for safer and more reliable surgery. In the case where the optical communication is performed, the communication unit 26 is provided with a photoelectric conversion module for converting an electrical signal into an optical signal. After the image signal is converted into the optical signal by the photoelectric conversion module, the signal is transmitted to the CCU 51 through the transmission cable 91.

In addition, the communication unit 26 receives a control signal for controlling the drive of the camera head 23 from the CCU 51. The control signal includes, for example, information regarding the imaging conditions, such as information for designating a frame rate of the captured image, information for designating an exposure value in imaging, and/or information for designating the magnification and the focus of the captured image. The communication unit 26 provides the received control signal to the camera head control unit 28.

Note that the control signal from the CCU 51 may also be transmitted through optical communication. In this case, the communication unit 26 is provided with a photoelectric conversion module that converts an optical signal into an electrical signal. After the control signal is converted into as electrical signal by the photoelectric conversion module, the signal is provided to the camera head control unit 28.

Note that the control unit 85 of the CCU 51 automatically sets the imaging conditions, such as the frame rate, the exposure value, the magnification, and the focus, based on the acquired image signal. That is, the endoscope 20 is provided with so-called AE (Auto Exposure) function, AF (Auto Focus) function, and AWB (Auto White Balance) function.

The camera head control unit 28 controls the drive of the camera head 23 based on the control signal from the CCU 51 received through the communication unit 26. For example, the camera head control unit 28 controls the drive of the imaging device of the imaging unit 27 based on the information for designating the frame rate of the captured image and/or the information for designating the exposure in imaging. In addition, for example, the camera head control unit 28 appropriately moves the zoom lens and the focus lens of the lens unit 25 through the drive unit 29 based on the information for designating the magnification and the focus of the captured image. The camera head control unit 28 may also have a function of storing information for identifying the barrel 21 and the camera head 23.

Note that the components, such as the lens unit 25 and the imaging unit 27, can be arranged in a highly airtight and waterproof sealed structure so that the camera head 23 can be resistant to the autoclave sterilization process.

Next, the functional configuration of the CCU 51 will be described. The communication unit 81 includes a communication apparatus that transmits and receives information to and from the camera head 23. The communication unit 81 receives an image signal from the camera head 23 transmitted through the transmission cable 91. On this occasion, the image signal can be suitably transmitted through optical communication as described above. In this case, the communication unit 81 is provided with a photoelectric conversion module that converts an optical signal into an electrical signal in accordance with the optical communication. The communication unit 81 provides the image signal converted into the electrical signal to the image processing unit 83.

In addition, the communication unit 81 transmits a control signal for controlling the drive of the camera head 23 to the camera head 23. The control signal may also be transmitted through the optical communication.

The image processing unit 83 applies various types of image processing to the image signal as raw data transmitted from the camera head 23. Examples of the image processing include various types of well-known signal processing, such as a development process, high-resolution processing (such as a band emphasizing process, super-resolution processing, an NR (Noise reduction) process, and/or an image stabilization process), and/or an enlargement process (electronic zoom process). The image processing unit 83 also executes a wave detection process of the image signal to perform AE, AF, and AWB.

The image processing unit 83 includes a processor, such as a CPU and a CPU, and the processor can operate according to a predetermined program to execute the image processing or the wave detection process. Note that in a case where the image processing unit 83 includes a plurality of GPUs, the image processing unit 83 appropriately divides the information regarding the image signal, and the plurality of GPUs execute the image processing in parallel.

The control unit 85 performs various types of control regarding the imaging of the surgical site by the endoscope 20 and regarding the display of the captured image. For example, the control unit 85 generates a control signal for controlling the drive of the camera head 23. On this occasion, in a case where the user inputs the imaging conditions, the control unit 85 generates a control signal based on the input of the user. Alternatively, in a case where the endoscope 20 has the AE function, the AF function, and the AWB function, the control unit 85 generates a control signal by appropriately calculating the optimal exposure value, the focal length, and the white balance according to the result of the wave detection process of the image processing unit 83.

In addition, the control unit 85 causes the display apparatus 53 to display an image of the surgical site based on the image signal after the image processing by the image processing unit 83. In this case, the control unit 85 uses various image recognition techniques to recognize various objects in the surgical site image.

For example, the control unit 85 can detect shapes, colors, and the like of the edges of the objects included in the surgical site image to recognize a surgical tool such as a forceps, a specific body part, bleeding, mist during the use of the energy treatment tool 33, and the like. When the control unit 85 causes the display apparatus 53 to display the image of the surgical site, the control unit 85 uses the recognition result to superimpose various types of surgery support information on the image of the surgical site. The surgery can be more safely and reliably advanced by superimposing and presenting the surgery support information to the surgeon 71.

The transmission cable 91 connecting the camera head 23 and the CCU 51 is an electrical signal cable corresponding to the communication of electrical signal, an optical fiber corresponding to the optical communication, or a composite cable of these.

Although the transmission cable 91 is used to perform wired communication in the example illustrated here, the communication between the camera head 23 and the CCU 51 may be wirelessly performed. In the case where the communication between the camera head 23 and the CCU 51 is wirelessly performed, the transmission cable 91 does not have to be installed in the operating room. This can eliminate the situation in which the movement of the medical staff in the operating room is obstructed by the transmission cable 91.

This completes the description of an example of the endoscopic surgery system 10 to which the technique according to the present disclosure can be applied.

Note that although the endoscopic surgery system 10 has been described as an example here, the system to which the technique according to the present disclosure can be applied is not limited to the example. For example, the technique according to the present disclosure may be applied to an inspection flexible endoscope system or a microsurgery system.

In the following description, the description of the example of the endoscopic surgery system 10 as an example according to the present technique will be continued. In the endoscopic surgery system 10 according to the present technique, a normal image and a special image can be acquired, and the acquired normal image and special image can be superimposed and presented to the surgeon.

Figure 3:
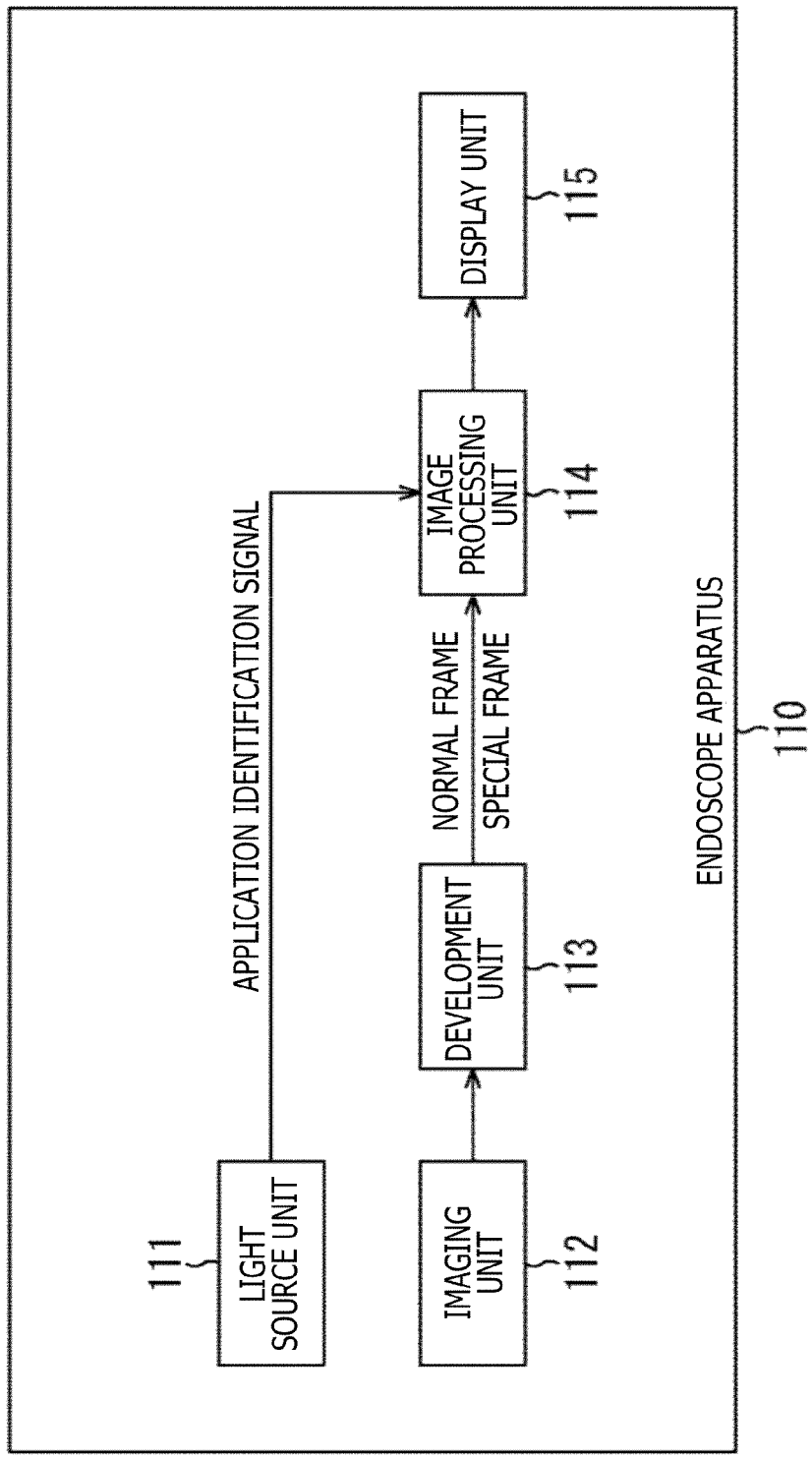
FIG. 3 is a block diagram illustrating a configuration example of an endoscope apparatus.

The configuration of the endoscopic surgery system will be described again to add description regarding the acquisition of the normal image and the special image and regarding the superimposition of the acquired normal image and special image. FIG. 3 is a diagram illustrating a configuration of an example of the endoscope apparatus with a function of acquiring the normal image and the special image, superimposing the acquired normal image and special image, and presenting the superimposed images.

Here, the normal image denotes an image captured by applying normal light, such as white light, to an organ or the like as a subject. Hereinafter, the normal image will also be referred to as a normal frame. The special image denotes an image captured by applying special light with a predetermined wavelength different from the normal light. Hereinafter, the special image will also be referred to as a special frame. Note that in capturing the special image, a fluorescent agent or the like that reacts to the application of the special light may be mixed or applied to a blood vessel (blood) or a lesion as a subject.

An endoscope apparatus 110 illustrated in FIG. 3 indicates a configuration example of an endoscope apparatus that images the normal frame and the special frame in time division, accurately positions and combines the frames, and displays a combined frame obtained as a result of the positioning and combining.

The endoscope apparatus 110 includes a light source unit 111, an imaging unit 112, a development unit 113, an image processing unit 114, and a display unit 115. The light source unit 111 corresponds to, for example, the light source apparatus 55 (FIG. 1) of the endoscopic surgery system 10. The imaging unit 112 corresponds to the imaging unit 27 (FIG. 2). The development unit 113 is included in the image processing unit 83 (FIG. 2). The image processing unit 114 corresponds to the image processing unit 83 (FIG. 2). The display unit 115 corresponds to the display apparatus 53 (FIG. 1).

For each frame to be imaged, the light source unit 111 switches the normal light, such as white light, and the special light of a predetermined wavelength and applies the light to the subject (such as an organ in the body). The light source unit 111 also outputs, to the image processing unit 114, an application identification signal indicating which one of the normal light and the special light is applied, for each frame to be imaged. Note that to apply the special light, an optical filter that transmits only a predetermined wavelength can be provided on the optical path of the normal light.

The imaging unit 112 images a subject in the state that the normal light or the special light is applied from the light source unit 111 and outputs an image signal obtained as a result of the imaging to the development unit 113. The development unit 113 applies a development process, such as mosaic processing, to the image signal input from the imaging unit 112 and outputs an image signal as a processing result (normal frame when normal light is applied, or special frame when special light is applied) to the image processing unit 114.

Here, the blood vessel and the lesion, such as a tumor, in the special frame are clearer than in the normal frame. However, the brightness of the entire frame is low, and the noise is high in the special frame. On the other hand, the brightness of the entire frame of the normal frame is higher than in the special frame, and the noise is lower than in the special frame. However, the blood vessel and the lesion, such as a tumor, are hard to distinguish.

The image processing unit 114 uses two normal frames at different imaging timing to detect a motion vector. The image processing unit 114 also performs motion correction of the special frame based on the motion vector detected from the normal frame and combines the normal frame and the special frame after the motion correction. The image processing unit 114 outputs, to the display unit 115, a combined frame obtained as a result of the combining.

The display unit 115 displays the combined frame.

<Imaging Timing of Normal Frame and Special Frame>

Figure 4:
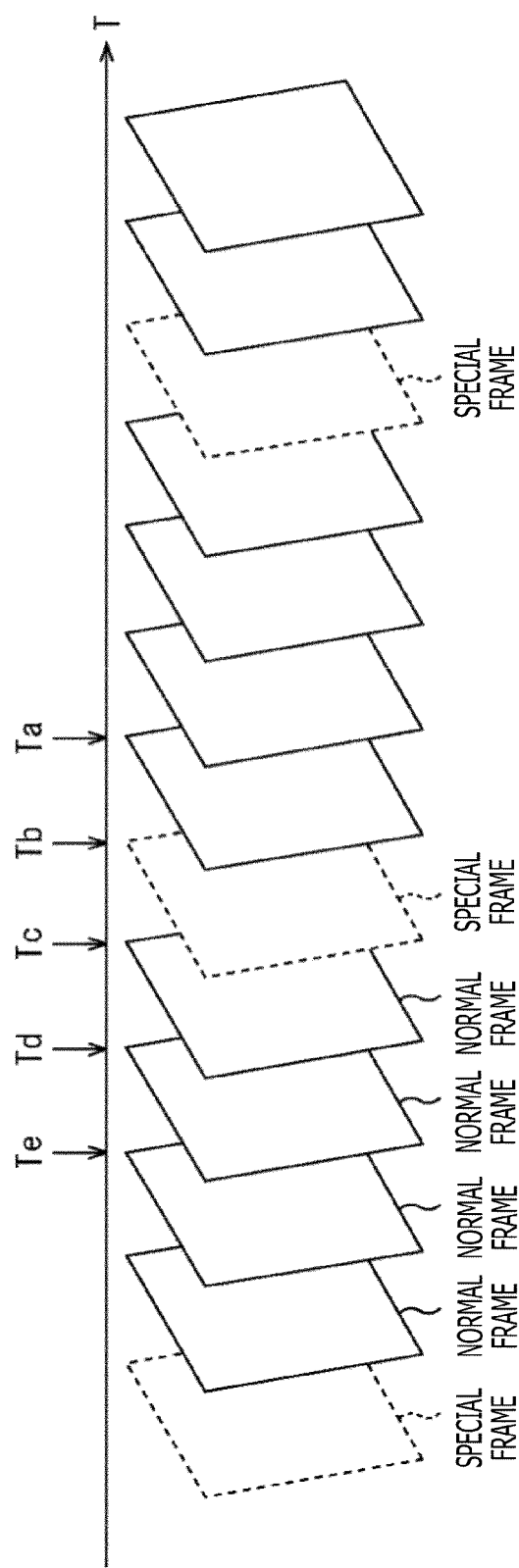
FIG. 4 is a diagram illustrating imaging timing of a normal frame and a special frame.

FIG. 4 illustrates an example of imaging timing of the normal frames and the special frames.

In the endoscope apparatus 110, the normal frames are continuously imaged for several frames, and the special frame is definitionally imaged in the meantime. For example, as illustrated in FIG. 4, the ratio of imaging the normal frames and the special frames is 4 to 1.

However, the ratio is not limited to 4 to 1, and the ratio may be changeable. Ta in FIG. 4 indicates the timing of the imaging of the normal frame one frame before the imaging of the special frame. Tb indicates the timing of the imaging of the special frame. Tc, Td, and Te indicate the timing of the imaging of the normal frames that are one frame, two frames, and three frames after the imaging of the special frame, respectively. Ta to Te are used to describe the detection of the motion vector described later.

<Configuration Example of Image Processing Unit 114>

Figure 5:
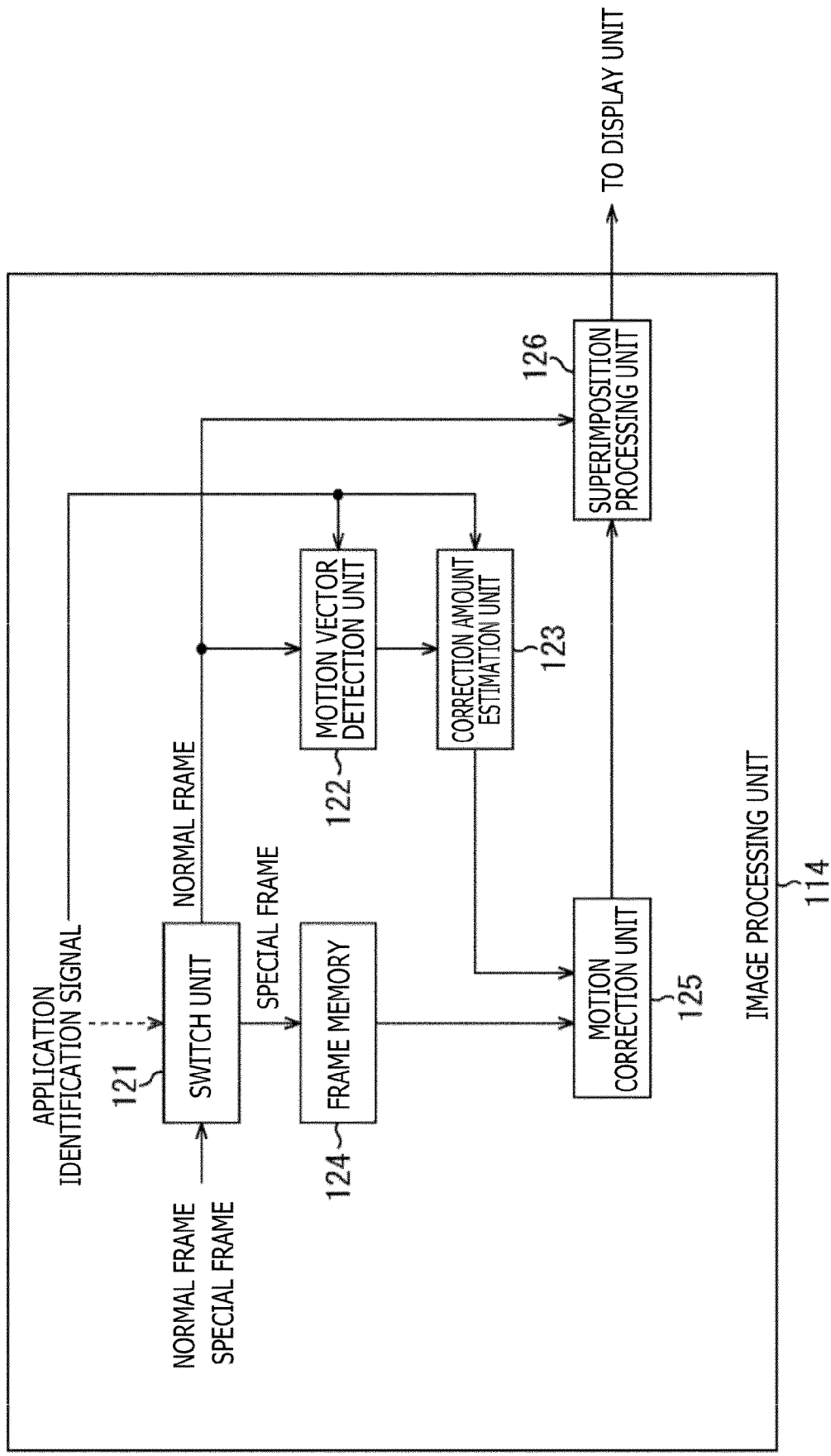
FIG. 5 is a block diagram illustrating a detailed configuration example of an image processing unit.

Next, FIG. 5 illustrates a configuration example of the image processing unit 114.

The image processing unit 114 includes a switch unit 121, a motion vector detection unit 122, a correction amount estimation unit 123, a frame memory 124, a motion correction unit 125, and a superimposition processing unit 126.

In the image processing unit 114, the normal frame and the special frame input from the development unit 113 in the earlier stage are input to the switch unit 121, and the application identification signal from the light source unit 111 is input to the switch unit 121, the motion vector detection unit 122, and the correction amount estimation unit 123.

The switch unit 121 determines whether or not the input from the development unit 113 is the special frame based on the application identification signal. The switch unit 121 outputs the frame to the motion vector-detection unit 122 and the superimposition processing unit 126 in a case where the input is not the special frame (but the normal frame). The switch unit 121 outputs the frame to the frame memory 124 in a case where the input is the special frame.

The motion vector detection unit 122 uses two normal frames with different imaging timing to detect the motion vector for each frame period and outputs the detected motion vector to the correction amount estimation unit 123.

The correction amount estimation unit 123 estimates an amount of motion correction of the special frame based on the motion vector detected by the motion vector detection unit 122 and outputs the estimated amount of motion correction to the motion correction unit 125. Note that the correction amount estimation unit 123 can correct the motion vector with a possibility of false detection based on continuously detected motion vectors and can estimate the amount of motion correction based on the corrected motion vector.

The frame memory 124 holds the special frame input from the switch unit 121 and supplies the held special frame to the motion correction unit 125 for each frame period. In addition, the frame memory 124 updates the held special frame in a case where the next special frame is input from the switch unit 121.

Note that a process may be executed in which, for example, an area where 3×3 dispersion or dynamic range in a small block is equal to or greater than a threshold is extracted, and a feature extraction frame representing the extraction result is generated. In addition, a process may be executed in which, for example, an area where the signal level of pixel is within a specific threshold, that is, an area with specific RGB level, is extracted, and a feature extraction frame representing the extraction result is generated. In addition, for example, a contour detection process, such as SNAKE, may be applied to a closed area (equivalent to a tumor or the like) to generate a feature extraction frame representing the result.

The motion correction unit 125 performs the motion correction of the special frame from the frame memory 124 based on the amount of motion correction input from the motion correction amount estimation unit 123 and outputs the special frame after the motion correction to the superimposition processing unit 126.

The superimposition processing unit 126 receives the normal frame and the special frame after the motion correction to generate a combined frame (superimposed frame) by executing a superimposition combining process and outputs the frame to the display unit 115 in the later stage.

<Configuration Example of Motion Vector Detection Unit 122>

Figure 6:
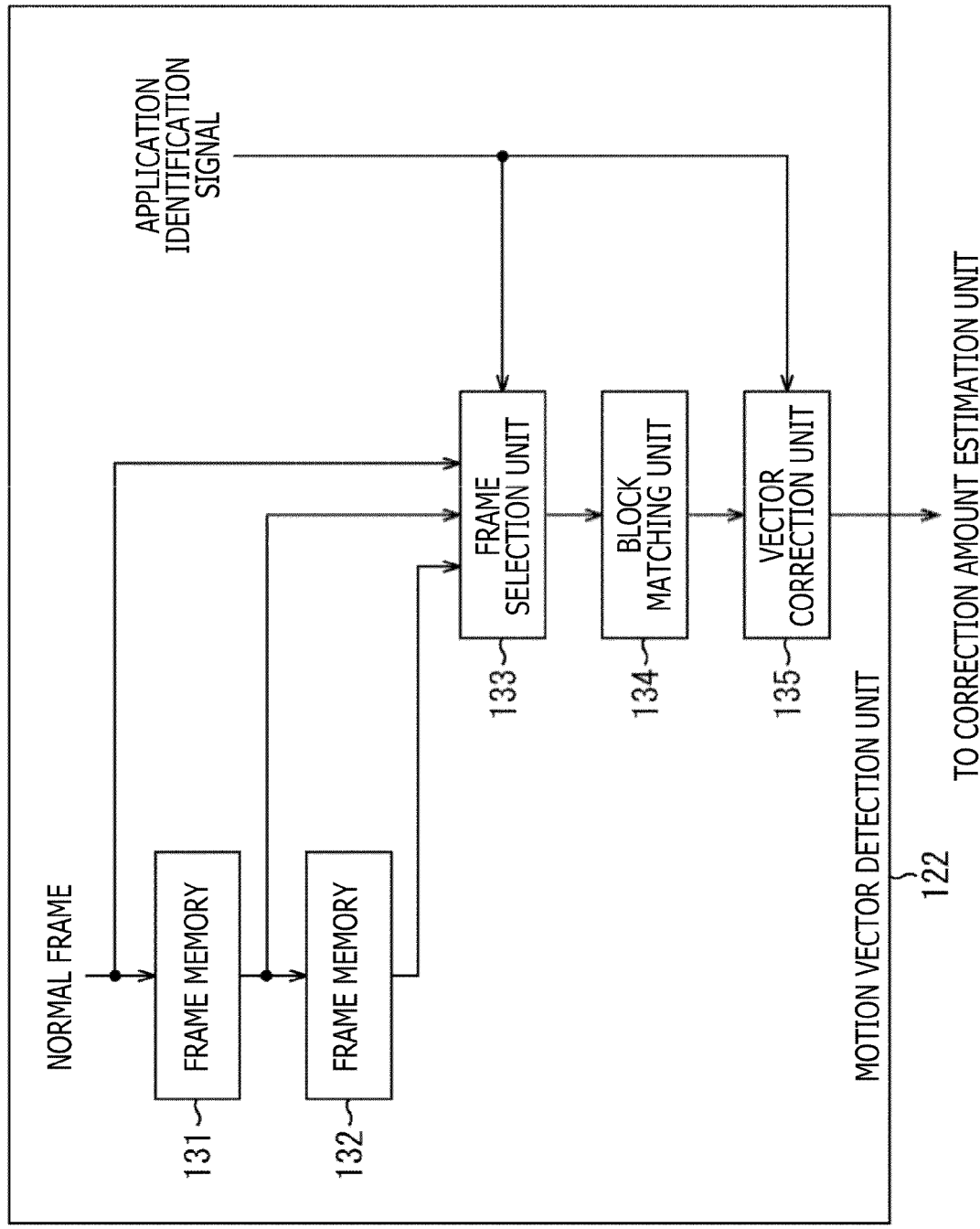
FIG. 6 is a block diagram illustrating a detailed configuration example of a motion vector detection unit.

FIG. 6 illustrates a configuration example of the motion vector detection unit 122. The motion vector detection unit 122 includes frame memories 131 and 132, a frame selection unit 133, a block matching unit 134, and a vector correction unit 135.

In the motion vector detection unit 122, the normal frame input from the switch unit 121 in the earlier stage is input to the fame memory 131 and the frame selection unit 133.

The frame memory 131 outputs the normal frame held at that point to the frame memory 132 and the frame selection unit 133 for each frame period and updates the held data with the normal frame input from the switch unit 121 in the earlier stage. Similarly, the frame memory 132 outputs the held normal frame to the frame selection unit 133 for each frame period and updates the held data with the normal frame input from the frame memory 131 in the earlier stage.

However, at the timing in which the normal frame is not input to the motion vector detection unit 122 in the frame period, the frame memory 131 outputs the normal frame held at that point to the later stage and clears the data held at that point.

At the next timing, the frame memory 131 does not output data to the later stage because there is no data held. The frame memory 132 outputs the normal frame held at that point to the later stage and clears the data held at that point.

Therefore, two or three normal frames with different imaging timing are input to the frame selection unit 133 at the same time.

In the case where two normal frames are input at the same time, the frame selection unit 133 outputs the two normal frames to the block matching unit 134. Furthermore, in the case where three normal frames are input at the same time, the frame selection unit 133 outputs two normal frames input from the frame memories 131 and 132 to the block matching unit 134. The block matching unit 134 executes a block matching process to detect the motion vector between the two normal frames.

The vector correction unit 135 determines the relationship between the two normal frames used for the motion vector based on the application identification signal. The vector correction unit 135 corrects the detected motion vector based on the relationship and outputs the motion vector to the correction amount estimation unit 123.

The correction of the motion vector by the vector correction unit 135 will be specifically described. In a case where the standard imaging time is Ta illustrated in FIG. 4 on the basis of the output from the frame memory 131, the normal frame one frame before the standard is input to the frame selection unit 133 from the frame memory 132, and the standard normal frame is input to the frame selection unit 133 from the frame memory 131. The motion vector is detected from the two normal frames. In this case, the vector correction unit 135 does not correct the motion vector.

In a case where the standard imaging timing is Tb illustrated in FIG. 4, the frame memory 131 does not output the frame because Tb is the imaging timing of the special frame. Furthermore, the normal frame one frame before the standard is input to the frame selection unit 133 from the frame memory 131, and the normal frame one frame after the standard is input to the frame selection unit 133 from the switch unit 121. The motion vector is detected from the two normal frames. In this case, the detected motion vector is a motion vector between the normal frames two frames away from each other. Therefore, the vector correction unit 135 multiplies the vertical and horizontal components of the detected motion vector by ½.

In a case where the standard imaging timing is Tc illustrated in FIG. 4, the standard normal frame is input to the frame selection unit 133 from the frame memory 131, and the normal frame one frame after the standard is input to the frame selection unit 133 from the switch unit 121. The motion vector is detected from the two normal frames. In this case, the directions of the detected motion vector are opposite, and the vector correction unit 135 multiplies the vertical and horizontal components of the detected motion vector by −1.

In a case where the standard imaging timing is Td illustrated in FIG. 4, the normal frame one frame before the standard is input to the frame selection unit 133 from the frame memory 132, the standard normal frame is input to the frame selection unit 133 from the frame memory 131, and the normal frame one frame after the standard is input to the frame selection unit 133 from the switch unit 121. The motion vector is detected from the two normal frames from the frame memories 131 and 132. In this case, the vector correction unit 135 does not correct the motion vector.

In a case where the standard imaging timing is Te illustrated in FIG. 4, the normal frame one frame before the standard is input to the frame selection unit 133 from the frame memory 132, the standard normal frame is input to the frame selection unit 133 from the frame memory 131, and the normal frame one frame after the standard is input to the frame selection unit 133 from the switch unit 121. The motion vector is detected from the two normal frames from the frame memories 131 and 132. In this case, the vector correction unit 135 does not correct the motion vector.

The vector correction unit 135 outputs the motion vector corrected in this way to the correction amount estimation unit 123 in the later stage.

<Image Combining Process of Image Processing Unit 114>

Figure 7:
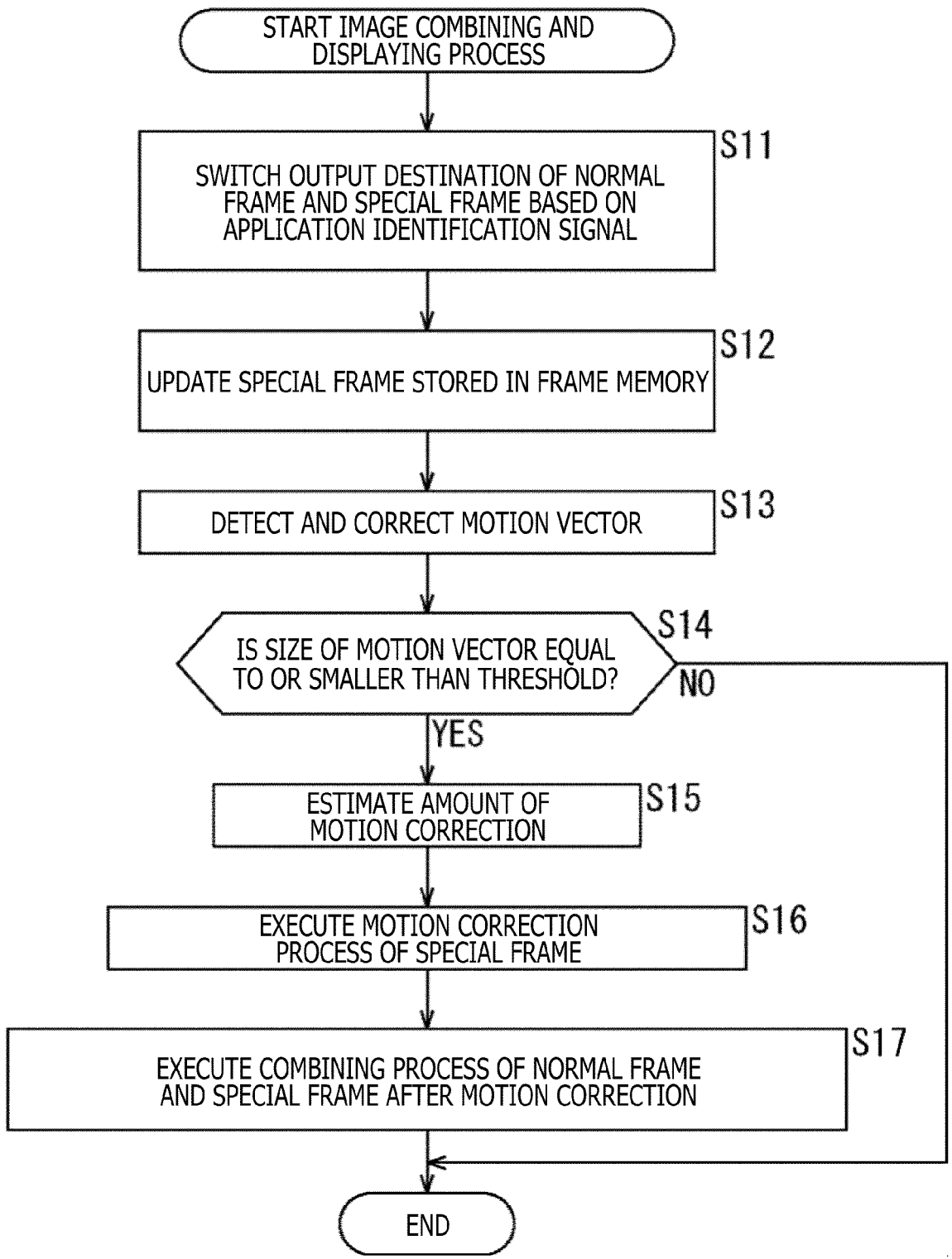
FIG. 7 is a flow chart describing an image combining process.

Next, an image combining process of the image processing unit 114 will be described with reference to FIG. 7. FIG. 7 is a flow chart describing an image combining process. The image combining process is executed for each frame period.

In step S11, the switch unit 121 determines whether or not the input from the development unit 113 is a special frame based on the application identification signal and outputs the special frame to the frame memory 124 in a case where the switch unit 121 determines that the input is a special frame. On the other hand, in a case where the switch unit 121 determines that the input is not a special frame (but a normal frame), the switch unit 121 outputs the normal frame to the motion vector detection unit 122 and the superimposition processing unit 126.

In step S12, the frame memory 124 supplies the special frame held at that point to the motion correction unit 125. Note that in a case where a special frame is input, from the switch unit 121, the held special frame is updated.

In step S13, the motion vector detection unit 122 uses two normal frames with different imaging timing to detect the motion vector and outputs the motion vector to the correction amount estimation unit 123. In step S14, the correction amount estimation unit 123 determines whether or not the detected motion vector is equal to or smaller than a predetermined threshold and advances the process to step S15 to use the motion vector for the motion correction in a case where the detected motion vector is equal to or smaller than the predetermined threshold. On the other hand, the motion vector is not used for the motion correction in a case where the detected motion vector is greater than the predetermined threshold. In this case, the image combining process corresponding to the imaging timing of this time ends.

In step S15, the correction amount estimation unit 123 estimates the amount of motion correction of the special frame based on the motion vector detected by the motion vector detection unit 122 and outputs the estimated amount of motion correction to the motion correction unit 125.

After the estimation of the amount of motion correction, the process proceeds to step S16. In step S16, the motion correction unit 125 performs the motion correction of the special frame from the frame memory 124 based on the amount of motion correction input from the motion correction amount estimation unit 123 and outputs the special frame after the motion correction to the superimposition processing unit 126. The subjects in the normal frame and the special frame input to the superimposition processing unit 126 are accurately positioned.

In step S17, the superimposition processing unit 126 uses the normal frame and the special frame after the motion correction to execute a superimposition combining process to thereby generate a combined frame and outputs the combined frame to the display unit 115 in the later stage.

As a result of the execution of the process, the endoscope apparatus 110 can detect the motion vector just by using the normal frame and can estimate the amount of motion correction after correcting the detected motion vector. The endoscope apparatus 110 can accurately execute the motion correction of the special frame. Therefore, the information of the special frame, such as a blood vessel and a tumor, can be accurately positioned with respect to the normal frame. This allows the user (such as a doctor performing a surgery) to accurately and clearly recognize the tumor part to be excised and the blood vessel part not to be excised.

The combined frame to be presented to the user is created based on the normal frame, and the combined frame with higher brightness and lower noise than the special frame can be presented to the user.

<Method of Providing Superimposed Image>

As described above, the normal frame and the special frame can be obviously superimposed (combined) to provide the combined frame to the user. The frames may also be processed into an image for presenting information to the user, and the image may be presented.

A fluorescent substance is injected into the body in order to visualize the flow of blood and lymph, the tumor site, and the like that are hard to determine based only on the image of the normal frame, and the special frame is imaged to observe the fluorescent substance as a fluorescence image.

In displaying the special frame, display, such as monochromatic display, single-color display, and color map display for changing the color according to the luminance of fluorescence, is selectively performed. Note that "selective" indicates a case in which the user selects the display, a case in which the display is selected based on predetermined conditions, or the like. In addition, it is difficult to visually recognize the situation around the fluorescent site just by displaying the special frame, and therefore, the special frame is also superimposed on the normal frame imaged at the same time to display the combined frame as described above.

Furthermore, according to the present technique, when the combined frame or the special frame is displayed, a correlation coefficient between frames of the normal frame and the special frame (correlation coefficient between pixels) is calculated, and the display method is switched according to the difference in the correlation coefficient. Hereinafter, the correlation coefficient and the display method will be further described. Note that in the following description, the display based on the correlation coefficient will be referred to as correlation display, and the frame displayed in the correlation display will be referred to as a correlation frame.

The correlation frame is, for example, a frame (image) that allows to easily recognize the difference in observation conditions by visualizing the difference in the correlation coefficient because the correlation coefficient of the normal frame and the special frame varies according to the difference in the observation conditions of the fluorescent substance.

The correlation frame can be generated as the combined frame, and the generation of the correlation frame can be basically similar to the generation of the combined frame described above (described with reference to FIG. 7 and the like). However, the difference is that the generation of the correlation frame includes processes, such as calculating the correlation coefficient and combining the frames based on the correlation coefficient, as part of the processes.

In the following description, the description of the points performed similarly to the generation of the combined frame will be appropriately omitted.

<Configuration of Superimposition Processing Unit>

Figure 8:
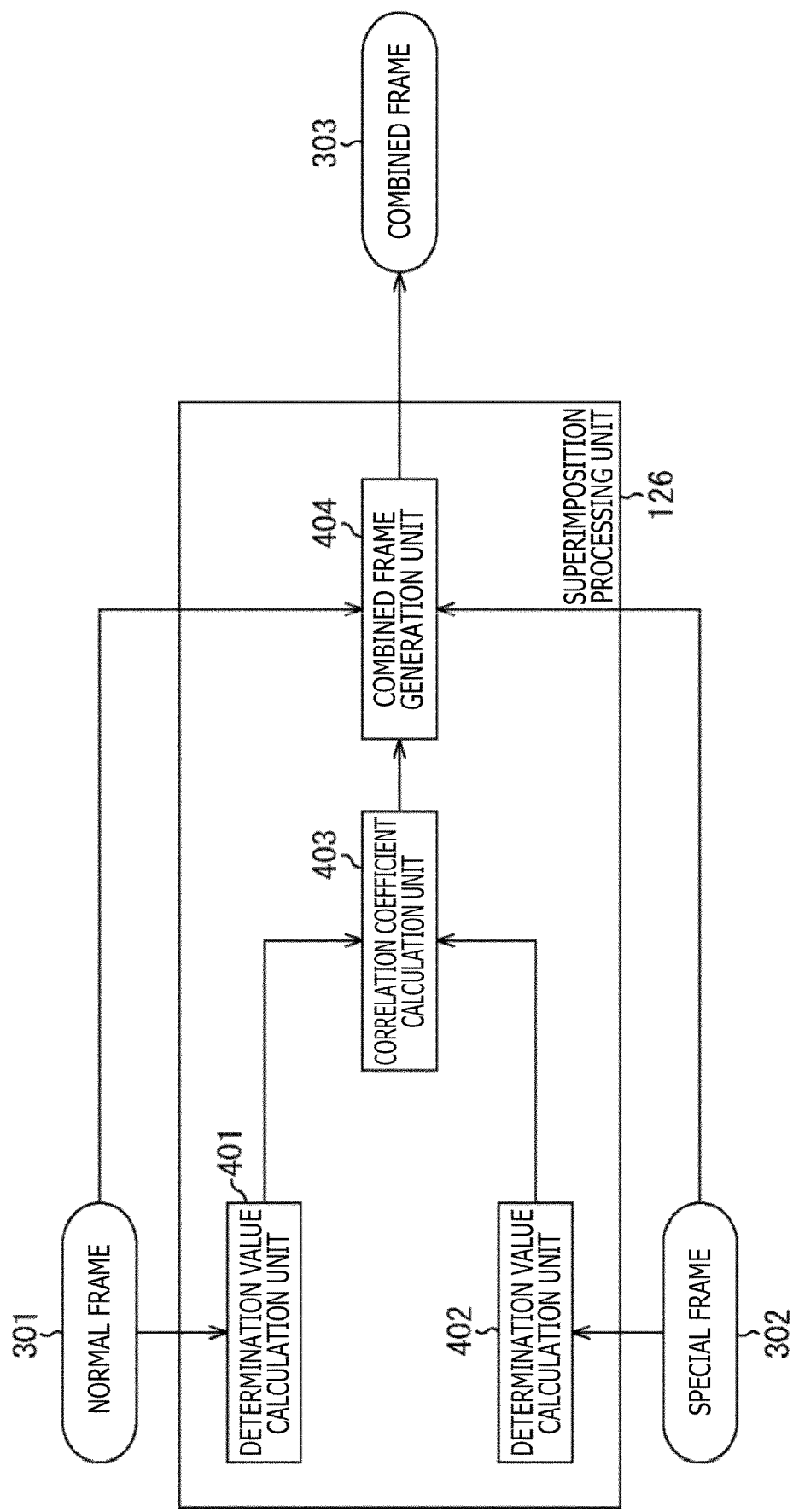
FIG. 8 is a diagram illustrating a configuration example of a superimposition processing unit.

FIG. 8 is a diagram illustrating a configuration example of the superimposition processing unit 126. The superimposition processing unit 126 includes a determination value calculation unit 401, a determination value calculation unit 402, a correlation coefficient calculation unit 403, and a combined frame generation unit 404.

A normal frame 301 is supplied to the determination value calculation unit 401. The determination value calculation unit 401 determines a probability of a predetermined site, such as a blood vessel and an affected part, in the normal frame 301 and calculates a determination value of the probability. Here, an example of a case of determining the probability of a blood vessel will be described.

For example, the determination value calculation unit 401 determines whether or not a predetermined area (pixel) in the normal frame 301 is a blood vessel and calculates a determination value indicating the probability of blood vessel. In the description here, the determination value is a value from 0.0 to 1.0. The higher the probability of blood vessel, the closer the value to 1.0.

Note that it may also be that the higher the probability of blood vessel, the closer the value to 0.0. In addition, the numeric values described here are an example, and the numeric values do not indicate that the application range of the present technique is limited to the numeric values. It is obvious that other numeric values may be used to execute the process.

A special frame 302 is supplied to the determination value calculation unit 402. The determination value calculation unit 402 determines a probability of blood vessel is the special frame 302 and calculates a determination value of the probability. For example, the determination value calculation unit 402 determines whether or not a predetermined area (pixel) in the special frame 302 is a blood vessel and calculates a determination value (value from 0.0 to 1.0) indicating the probability of blood vessel.

Note that the special frame 302 supplied to the determination value calculation unit 402 is a frame with the position adjusted relative to the normal frame 301 in a process as described above. Therefore, whether or not the blood vessel is imaged can be determined for the same part in the normal frame 301 and the special frame 302, and the determination value can be calculated.

The determination value from the determination value calculation unit 401 (referred to as determination value A) and the determination value from the determination value calculation unit 402 (referred to as determination value B) are supplied to the correlation coefficient calculation unit 403. The correlation coefficient calculation unit 403 multiplies the determination value A by the determination value B to calculate the correlation coefficient, for example. Note that the method of obtaining the correlation coefficient is an example, and the correlation coefficient may be obtained by operation other than the multiplication of the determination value A and the determination value B.

In addition, although the details are not described here, ZNCC (zero-mean normalized cross-correlation), SSIM (Structural Similarity), or the like may be used to calculate the correlation coefficient. In addition, the correlation coefficient is calculated for each pixel or each area (block) in a predetermined size.

As for a part where the blood vessel is imaged in the normal frame 301, the probability that the blood vessel is also imaged in the special frame 302 is high. Therefore, the correlation coefficient is a high value. On the other hand, there is a possibility that the blood vessel is imaged in the special frame 302 even for a part where the blood vessel is not imaged in the normal frame 301. The correlation coefficient of such a part is a low value. The correlation coefficient is supplied to the combined frame generation unit 404.

The normal frame 301, the special frame 302, and the correlation coefficient from the correlation coefficient calculation unit 403 are supplied to the combined frame generation unit 404. The combined frame generation unit 404 combines the normal frame 301 and the special frame 302 based on the correlation coefficient and generates a combined frame.

Note that as described later, the user may be able to set which one of the normal frame, the special frame, and the correlation frame is to be displayed.

In the case where the user can set the frame to be displayed, the combined frame generation unit 404 does not execute the combining process and outputs the supplied normal frame 301 to the later stage (display unit 115) when the display of the normal frame is set. Alternatively, the image processing unit 148 (FIG. 4) may output the normal frame 301 to the later stage (display unit 115) without supplying the normal frame 301 to the superimposition processing unit 126 (such a path may be provided).

Similarly, in the case where the display of the special frame is set, the combined frame generation unit 404 does not execute the combining process and outputs the supplied special frame 302 to the later stage (display unit 115). Alternatively, the image processing unit 148 (FIG. 4) may output the special frame 302 to the later stage (display unit 115) without supplying the special frame 302 to the superimposition processing unit 126 (such a path may be provided).

<Calculation of Determination Value>

The calculation of the determination values of the determination value calculation unit 401 and the determination value calculation unit 402 will be further described. First, the method of calculating the determination value A in the determination value calculation unit 401 that calculates the determination value from the normal frame 301 will be further described.

Figure 9:
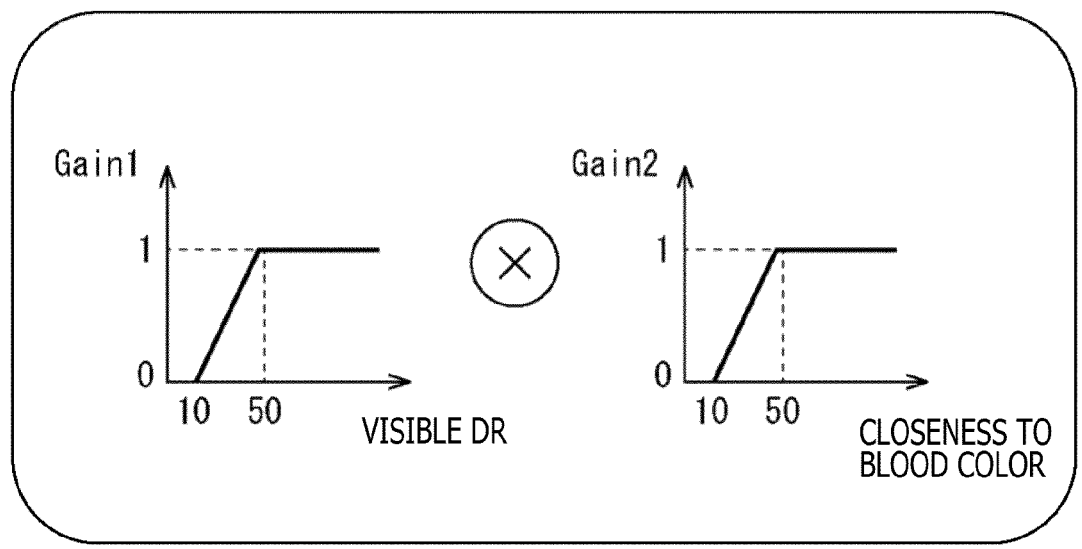
FIG. 9 is a diagram for describing calculation of a determination value.

As illustrated in FIG. 9, the determination value calculation unit 401 calculates a gain 1 (Gain1) and a gain 2 (Gain2) and multiplies the gain 1 by the gain 2 to calculate the determination value A. The gain 1 is a value calculated based on the size of a DR (Dynamic Range) (hereinafter, referred to as visible DR) in the normal frame 301 imaged under visible light. The visible DR can be, for example, a difference between a maximum value and a minimum value of pixel values in pixels around a pixel to be processed (pixel of interest).

The diagram on the left in FIG. 9 is a graph representing a relationship between the visible DR and the gain 1. The horizontal axis indicates the visible DR, and the vertical axis indicates the gain 1. When the value of the visible DR is 10 to 50, the value of the gain 1 transitions from 0.0 to 1.0 according to a linear function. Furthermore, in a case where the visible DR is equal to or smaller than 10, the gain 1 is 0.0. In a case where the visible DR is equal to or greater than 50, the gain 1 is 1.0.

For example, when the blood vessel and the surroundings of the blood vessel are compared, the blood vessel is brighter than the surroundings, or the red color of the blood vessel is darker than the surroundings. Therefore, the difference between the pixel values of the blood vessel and the surroundings of the blood vessel is large. That is, the visible DR may be large in such an area. Therefore, as illustrated in the diagram on the left in FIG. 9, the gain 1 is calculated based on a function in which the value of the gain 1 increases with an increase in the visible DR.

In addition, a function as illustrated in the diagram on the right in FIG. 9 is used to calculate the gain 2. The gain 2 is a value calculated based on the closeness to the blood color. The diagram on the right in FIG. 9 is a graph representing a relationship between the closeness (value representing the closeness) to the blood color and the gain 2. The horizontal axis indicates the closeness to the blood color (degree of similarity to blood color), and the vertical axis indicates the gain 2.

In the graph illustrated in the diagram on the right in FIG. 9, when the value representing the closeness to the blood color is a value from 10 to 50, the value of the gain 2 transitions from 0.0 to 1.0 according to a linear function. Furthermore, in a case where the value representing the closeness to the blood color is equal to or smaller than 10, the gain 2 is 0.0. In a case where the value representing the closeness to the blood color is equal to or greater than 50, the gain 2 is 1.0.

In the normal frame 301, the larger the visible DR and the closer the color to the blood vessel color, the higher the probability of blood vessel. In such an area (pixel) with high probability of blood vessel, the determination value A is calculated by multiplying the gain 1 by the gain 2 so that the determination value A is a high value (in this case, value close to 1.0).

Note that a correlation map regarding the gain 1 may be created from the gain 1, and a correlation map regarding the gain 2 may be created from the gain 2. The maps may be used to calculate the determination value A. In addition, a map regarding the determination value A may be created to calculate the correlation coefficient.

Figure 10:
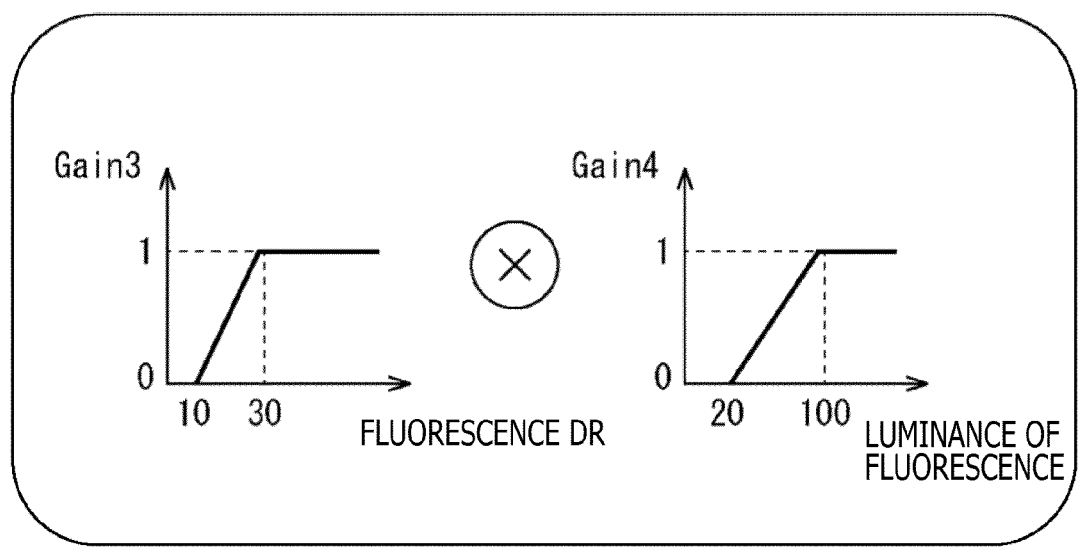
FIG. 10 is a diagram for describing calculation of a determination value.

The determination value calculation unit 402 calculates a gain 3 (Gain3) and a gain 4 (Gain4) and multiplies the gain 3 by the gain 4 as illustrated in FIG. 10 to calculate the determination value B. The gain 3 is a value calculated based on the size of a DR (Dynamic Range) of fluorescence. The DR of fluorescence can be, for example, a difference between a maximum value and a minimum value of pixel values in pixels around a pixel to be processed (pixel of interest).

The diagram on the left in FIG. 10 is a graph representing a relationship between the DR (hereinafter, referred to as fluorescence DR) of the special frame imaged under fluorescence and the gain 3. The horizontal axis indicates the fluorescence DR, and the vertical axis indicates the gain 3. When the value of the fluorescence DR is 10 to 30, the value of the gain 3 transitions from 0.0 to 1.0 according to a linear function. In addition, in a case where the fluorescence DR is equal to or smaller than 10, the gain 3 is 0.0. In a case where the fluorescence DR is equal to or greater than 30, the gain 3 is 1.0.

For example, when the blood vessel and the surroundings of the blood vessel are compared, the blood vessel provided with the fluorescent agent is brighter than the surroundings, or the color of the blood vessel is darker. Therefore, the difference between the pixel values of the blood vessel and the surroundings of the blood vessel is large. That is, the fluorescence DR may be large. Therefore, as illustrated in the diagram on the left in FIG. 10, the gain 3 is calculated based on a function in which the value of the gain 3 increases with an increase in the fluorescence DR.

In addition, a function as illustrated in the diagram on the right in FIG. 10 is used to calculate the gain 4. The gain 4 is a value calculated based on the luminance of the pixel to be processed (luminance of fluorescence). The diagram on the right in FIG. 10 is a graph representing a relationship between the luminance of fluorescence and the gain 4. The horizontal axis indicates the luminance of fluorescence, and the vertical axis indicates the gain 4. Note that in the case where the process is executed for each area, an average value or the like of the luminance values of the pixels in the area to be processed is used to execute the process.

In the graph illustrated in the diagram on the right in FIG. 10, when the value of the luminance of fluorescence is 20 to 100, the value of the gain 4 transitions from 0.0 to 1.0 according to a linear function. In addition, in a case where the luminance of fluorescence is equal to or smaller than 20, the gain 4 is 0.0. In a case where the luminance of fluorescence is equal to or greater than 100, the gain 4 is 1.0.

In the special frame 302, the larger the fluorescence DR and the higher the luminance, the higher the probability of blood vessel. In such an area (pixel) with high probability of blood vessel, the determination value B is calculated by multiplying the gain 3 by the gain 4 so that the determination value B is a high value (in this case, value close to 1.0).

Note that a correlation map regarding the gain 3 may be created from the gain 3, and a correlation map regarding the gain 4 may be created from the gain 4. The maps may be used to calculate the determination value B. In addition, a map regarding the determination value B may be created to calculate the correlation coefficient.

The correlation coefficient is calculated by multiplying the determination value A by the determination value B.

In the description here, the determination value A is supplied from the determination value calculation unit 401 to the correlation coefficient calculation unit 403. The determination value B is supplied from the determination value calculation unit 402 to the correlation coefficient calculation unit 403. The correlation coefficient calculation unit 403 multiplies the determination value A by the determination value B to calculate the correlation coefficient.

The gain 1 and the gain 2 may be supplied from the determination value calculation unit 401 to the correlation coefficient calculation unit 403. The gain 3 and the gain 4 may be supplied from the determination value calculation unit 402 to the correlation coefficient calculation unit 403. The correlation coefficient calculation unit 403 may multiply the gain 1, the gain 2, the gain 3, and the gain 4 to calculate the correlation coefficient.

The correlation coefficient indicates a high numeric value at a part with fluorescence where the blood vessel can be seen under visible light and indicates a low numeric value at a part with fluorescence where the blood vessel cannot be seen under visible light, for example. The calculation of the correlation coefficient in the correlation coefficient calculation unit 403 is adjusted to satisfy such a relationship.

<Process of Superimposition Processing Unit 126>

Figure 11:
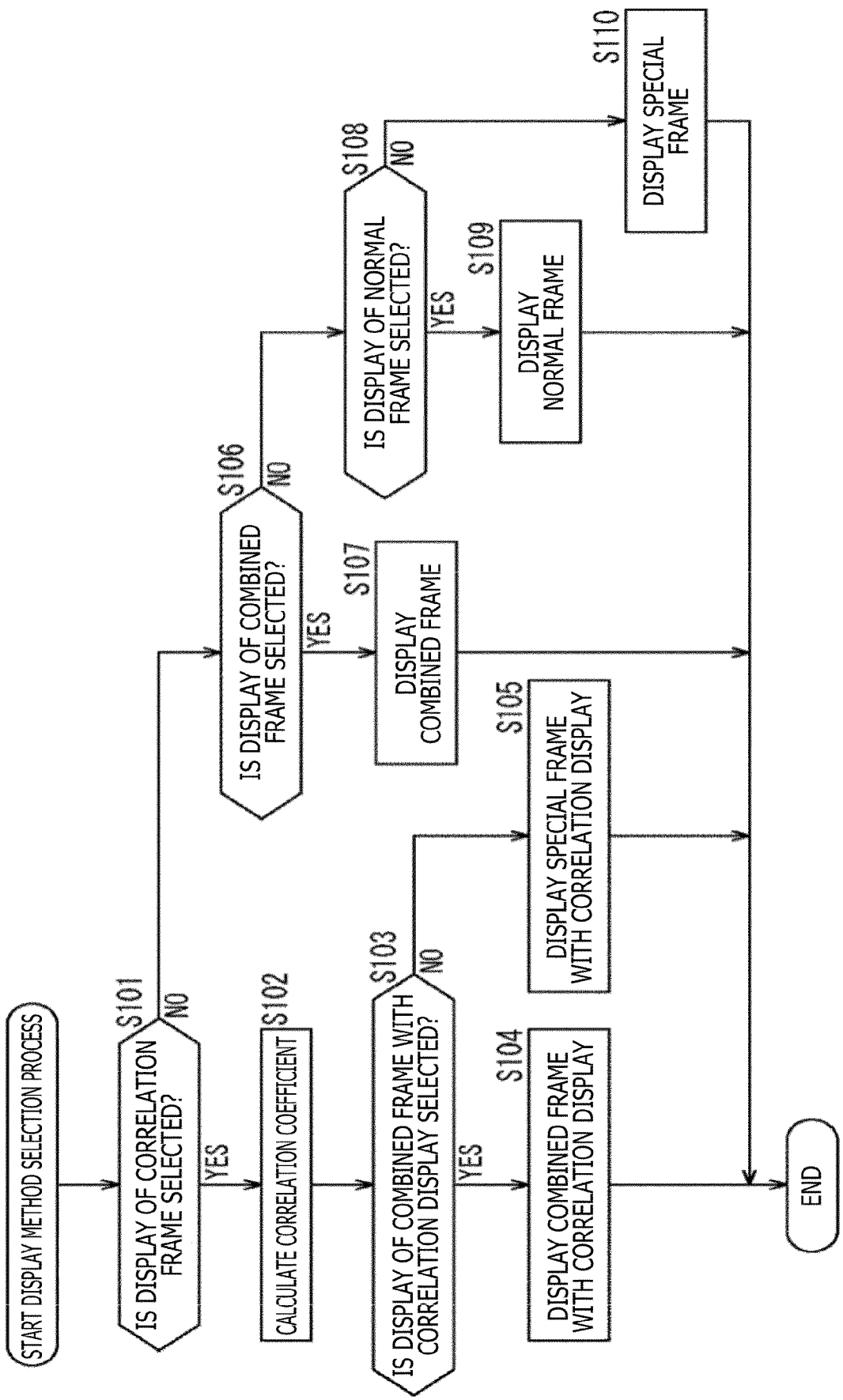
FIG. 11 is a flow chart for describing a process regarding display.

The process executed by the superimposition processing unit 126 will be further described with reference to a flow chart of FIG. 11.

In step S101, whether or not the display of the correlation frame is selected is determined. For example, the user can select the frame (image) displayed on the display unit 115 (FIG. 3), and the frame selected by the user is displayed.

In the example described here, the frames that can be selected by the user include a correlation frame, the combined frame, the normal frame, and the special frame.

The correlation frame is a frame after the image processing using the correlation coefficient. As described later, examples of the correlation frame include a case in which the correlation display is performed for the combined frame and a case in which the correlation display is performed for the special frame. The user can select and display one of the two correlation frames. Hereinafter, the former will be referred to as a combined frame with correlation display, and the latter will be referred to as a special frame with correlation display.

In step S101, whether or not the display of the correlation frame is selected is determined, and the process proceeds to step S102 in a case where it is determined that the display of the correlation frame is selected.

Note that the user can switch the displayed frame during the surgery, such as switching the display from the correlation frame to the normal frame, and the user can use desirable display to perform the surgery. Therefore, the process of the flow chart illustrated in FIG. 11 is repeatedly executed during the surgery.

In step S102, the correction coefficient is calculated. As described with reference to FIGS. 8 to 10, the correlation coefficient is calculated in the process of each of the determination value calculation unit 401, the determination value calculation unit 402, and the correlation coefficient calculation unit 403, and the correlation coefficient is supplied to the combined frame generation unit 404.

In step S103, whether or not the display of the combined frame with correlation display is selected is determined. In a case where it is determined that the display of the combined frame with correlation display is selected in step S103, the process proceeds to step S104.

In step S104, the combined frame with correlation display is displayed on the display unit 115. In this case, the combined frame generation unit 404 of the superimposition processing unit 126 superimposes the normal frame 301 and the special frame 302 and applies image processing based on the correlation coefficient to generate the combined frame with correlation display.

Figure 12:
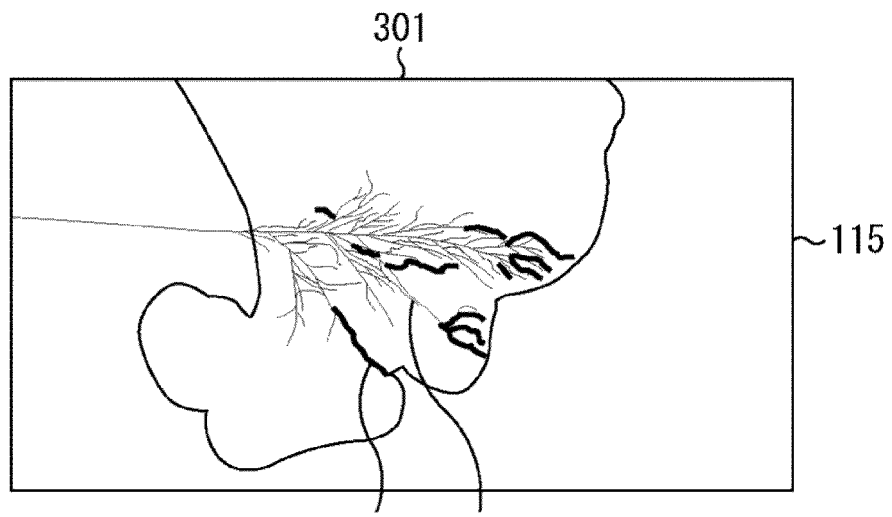
FIG. 12 is a diagram illustrating an example of a displayed screen.

FIG. 12 illustrates an example of the combined frame with correlation display. The display unit 115 displays a combined frame in which the special frame 302 is superimposed on the normal frame 301. Furthermore, a part indicated by a thick line in FIG. 12 is a correlation display part 501, and the correlation display part 501 is displayed in the case of the display with correlation display.

An area with a high value of correlation coefficient is displayed as the correlation display part 501. In addition, for example, blood vessels, affected parts, and the like (hereinafter, an example of blood vessel will be described) imaged in the special frame 302 and not imaged in the normal frame 301 have high values of correlation coefficient.

Therefore, the correlation display part 501 is a blood vessel imaged in the special frame 302, and in a case where the display of the correlation frame is not selected, the correlation display part 501 is a part displayed similarly to other blood vessels of the special frame 302.

Although the correlation display part 501 is indicated by a thick line in FIG. 12 to distinguish the correlation display part 501 from the blood vessels other than the correlation display part 501 for the convenience of description, the correlation display part 501 is actually displayed in thickness of the imaged blood vessel.

The correlation display part 501 (part with low correlation, or part with low correlation coefficient in this case) and the part other than the correlation display part 501 (part with high correlation, or part with high correlation coefficient in this case) can be displayed in different colors. For example, the correlation display part 501 (fluorescence area with low correlation coefficient) can be displayed in green, and the part other than the correlation display part 501 (fluorescence area with high correlation coefficient) can be displayed in magenta.

In addition, the parts may be displayed in colors according to the correlation coefficients, instead of displaying the parts in single colors such as green and magenta. For example, in a case where the correlation coefficient is a value close to 0.0, the correlation display part 501 may be purple. In a case where the correlation coefficient is a value close to 1.0, the correlation display part 501 may be green. The color display of the correlation display part 501 may be gradually changed from purple to green with an increase in the correlation coefficient from 0.0 to 1.0.

In a case where the correlation coefficient is a value close to 0.0, the blood vessel can be seen in the special frame 302 (image captured under fluorescence), but cannot be seen in the normal frame 301 (image captured under visible light). Such a part (correlation display part 501) imaged only in the special frame 302 as displayed in a color, purple here, that allows to clearly recognize that.

In a case where the correlation coefficient is a value close to 1.0, the blood vessel can be seen in the special frame 302 (image captured under fluorescence) and can also be seen in the normal frame 301 (image captured under visible light). Such a blood vessel may be displayed in green. In addition, the color of green can also be a display color of the part of the special frame 302 other than the correlation display part 501.

In other words, the color of the blood vessel or the like in the case where the correlation coefficient is a value close to 1.0 and the color of the blood vessel or the like imaged in the special frame 302 when only the special frame 302 is displayed can be the same color. The display color allows to clarify the difference between, for example, the display of the special frame 302 with correlation display and the display of the special frame 302 without correlation display, and the amount of information provided to the user can be increased.

Figure 13:
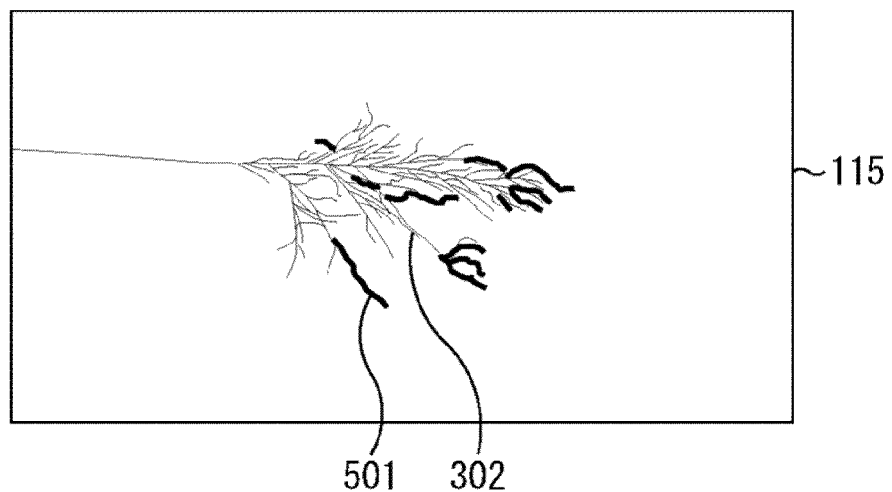
FIG. 13 is a diagram illustrating an example of the displayed screen.

For example, when the display of the special frame 302 with correlation display (with display of correlation display part 501) is instructed among the correlation frames illustrated in FIG. 12, an image as illustrated in FIG. 13 is displayed. When the display of the special frame 302 without correlation display is instructed, an image as illustrated in FIG. 14 is displayed.

As for the special frame 302 with correlation display illustrated in FIG. 13, the special frame 302 is displayed on the display unit 115, and the correlation display part 501 is further displayed in a predetermined color. The correlation display part 501 is displayed in, for example, purple, and the part (such as blood vessel) of the special frame 302 other than the correlation display part 501 is displayed in, for example, green.

Figure 14:
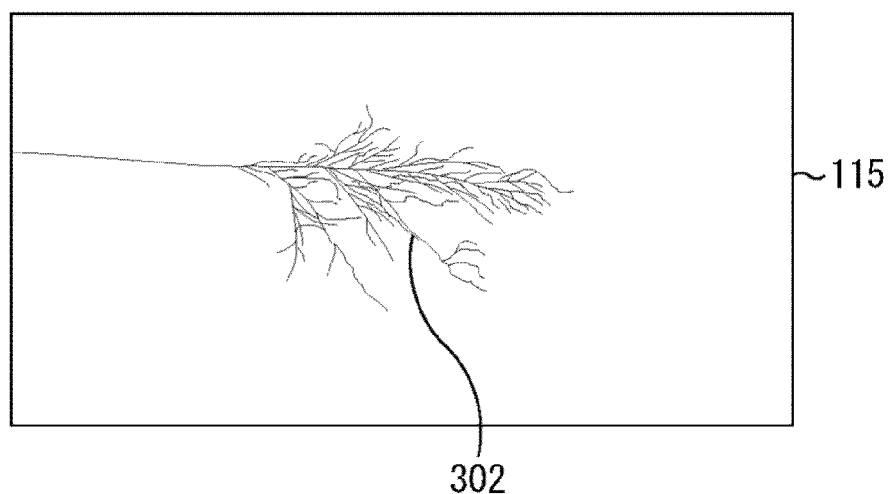
FIG. 14 is a diagram illustrating an example of the displayed screen.

As for the special frame 302 without correlation display illustrated in FIG. 14, the special frame 302 is displayed on the display unit 115. The part of the correlation display part 501 displayed when there is the correlation display is also displayed in, for example, green which is the same as the part (such as blood vessel) of the special frame 302 other than the correlation display part 501. In other words, the fluorescence parts of the special frame 302 without correlation display are displayed in the same color.

For example, in a case where the display of the special frame 302 without correlation display is switched to the display of the special frame 302 with correlation display, the display of the correlation display part 501 is switched from green to purple.

For example, the correlation display part 501 is a blood vessel not imaged in the normal frame 301, but imaged in the special frame 302 because the blood vessel is at a deep position. For example, when the user wants to know the blood vessel at a deep position, the user can switch the display of the special frame 302 without correlation display to the display of the special frame 302 with correlation display to switch the display (switch the display color) of the part of the correlation display part 501. Therefore, the user can recognize the blood vessel at a deep position.

In this way, the display of the correlation display part 501 allows the user to visually recognize the difference in observation conditions. Examples of the difference in observation conditions include the depth of the location of the blood vessel, the thickness of the blood vessel wall, and the characterization of the tissue up to the blood vessel. In other words, the correlation coefficient is a value that depends on the depth of the location of the blood vessel, the thickness of the blood vessel wall, and the characterization of the tissue up to the blood vessel, and the correlation display is performed based on the value.

The flow chart of FIG. 11 will be described again. In step S104, the combined frame with correlation display as illustrated in FIG. 12 is displayed on the display unit 115, for example.

On the other hand, in a case where it is determined that the display of the combined frame with correlation display is not selected in step S103, the process proceeds to step S105. In step S105, the special frame 302 with correlation display is displayed on the display unit 115. In this case, although the display of the correlation frame is selected in step S101, the display of the combined frame with correlation display is not selected. Therefore, the special frame with correlation display is displayed.

In step S105, the special frame 302 with correlation display as illustrated in FIG. 13 is displayed on the display unit 115, for example. The special frame 302 with correlation display is an image in which the part corresponding to the correlation display part 501 of the special frame 302 is displayed in a color different from the other parts.

Note that although there is no choice of displaying the normal frame 301 with correlation display in the example described here, such a choice may be provided, and the normal frame 301 with correlation display may be displayed. In a case where the choice is selected, the correlation display part 501 is superimposed on the normal frame 301, and such an image is displayed on the display unit 115.

On the other hand, in a case where it is determined that the display of the correlation frame is not selected in step S101, the process proceeds to step S106. In step S106, whether or not the display of the combined frame is selected is determined. In a case where it is determined that the display of the combined frame is selected in step S106, the process proceeds to step S107.

In step S107, the combined frame 303 is displayed on the display unit 115. For example, the combined frame 303 generated by executing the process of the flow chart illustrated in FIG. 7 is displayed on the display unit 115.

On the other hand, in a case where it is determined that the display of the combined frame is not selected in step S106, the process proceeds to step S108. In step S108, whether or not the display of the normal frame is selected is determined.

In a case where it is determined that the display of the normal frame is selected in step S108, the process proceeds to step S109. In step S109, the normal frame 301 is displayed on the display unit 115.

On the other hand, in a case where it is determined that the display of the normal frame is not selected in step S108, the process proceeds to step S110. In step S110, the special frame 302 is displayed on the display unit 115. The special frame 302 displayed in step S110 is an image as illustrated in FIG. 14, and the correlation display part 501 is not displayed in the image.

In this way, according to the present technique, the image selected by the user can be displayed. In addition, the normal frame 301 imaged under normal light, such as visible light, and the special frame 302 imaged under special light, such as fluorescence, can be combined to display the combined frame 303.

Furthermore, the part with strong correlation between the normal frame 301 and the special frame 302 and the part with weak correlation can be displayed differently. That is, according to the present technique, the correlation display part 501 can be displayed. Displaying the correlation display part 501 can provide an image that allows to easily recognize the difference between the normal frame 301 and the special frame 302, in other words, the difference in observation conditions, and can present more information to the user.

Note that although the correlation display part 501 and the part other than the correlation display part 501 are displayed in different colors in the embodiment described above, other display systems may also be applied. For example, the correlation display part 501 and the part other than the correlation display part 501 may be displayed in different brightness.

In addition, the correlation display part 501 may be displayed in a flashing state. In addition, the degree of emphasis in emphasizing the correlation display part 501 more than the other parts may be any display. In addition, the color, the brightness, the flashing state, the degree of emphasis, and the like may be switched by the user, or a mechanism for switching them may be provided based on some conditions.

In addition, the color, the brightness, the flashing state, the degree of emphasis, and the like may be switched in stages according to the correlation coefficient as in the case where the correlation display part 501 is displayed in the color according to the correlation coefficient as described above.

Note that although the correlation display is performed while capturing the images in real time in the example described in the embodiment, the present technique can also be applied to a case in which the correlation display is performed when recorded image data is reproduced.

<Recording Medium>

The series of processes described above can be executed by hardware or can be executed by software. In the case where the series of processes are executed by software, a program included in the software is installed on a computer. Here, examples of the computer include a computer incorporated into dedicated hardware and a general-purpose personal computer or the like that can execute various functions by installing various programs.

Figure 15:
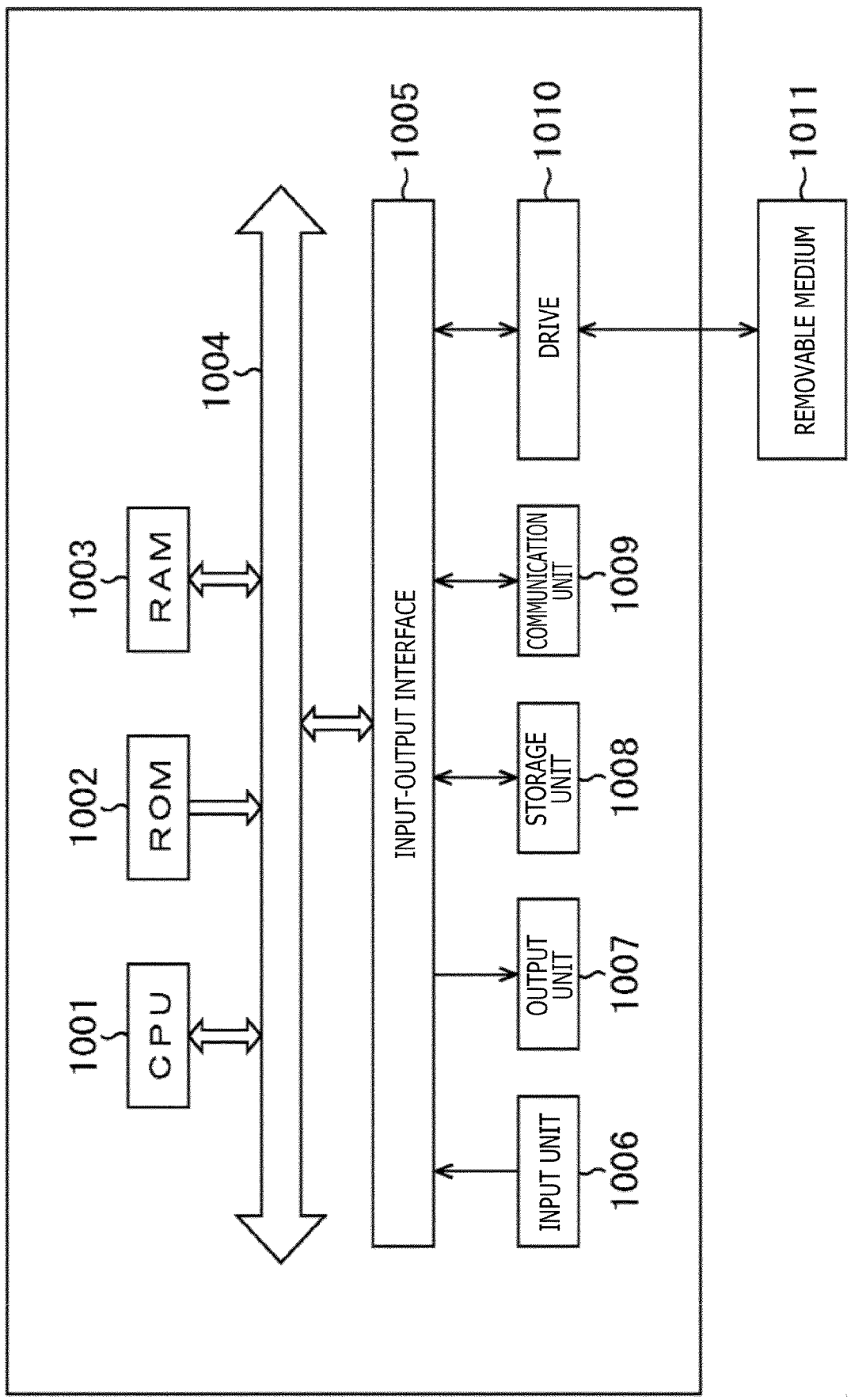
FIG. 15 is a diagram for describing a recording medium.

FIG. 15 is a block diagram illustrating a configuration example of the hardware of the computer that uses a program to execute the series of processes. In the computer, a CPU (Central Processing Unit) 1001, a ROM (Read Only Memory) 1002, and a RAM (Random Access Memory)

1003 are connected to each other through a bus 1004. An input-output interface 1005 is also connected to the bus 1004. An input unit 1006, an output unit 1007, a storage unit 1008, a communication unit 1009, and a drive 1010 are connected to the input-output interface 1005.

The input unit 1006 includes a keyboard, a mouse, a microphone, and the like. The output unit 1007 includes a display, a speaker, and the like. The storage unit 1008 includes a hard disk, a non-volatile memory, and the like. The communication unit 1009 includes a network interface and the like. The drive 1010 drives a removable medium 1011, such as a magnetic disk, an optical disk, a magneto-optical disk, and a semiconductor memory.

In the computer configured in this way, the CPU 1001 loads, for example, a program stored in the storage unit 1008 to the RAM 1003 through the input-output interface 1005 and the bus 1004 to execute the program to thereby execute the series of processes.

The program executed by the computer (CPU 1001) can be provided by, for example, recording the program in the removable medium 1011 as a package medium or the like. The program can also be provided through wired or wireless transmission medium, such as a local area network, the Internet, and digital satellite broadcasting.

In the computer, the removable medium 1011 can be mounted on the drive 1010 to install the program on the storage unit 1008 through the input-output interface 1005. In addition, the communication unit 1009 can receive the program through a wired or wireless transmission medium to install the program on the storage unit 1008. Furthermore, the program can be installed in advance on the ROM 1002 or the storage unit 1008.

Note that the program executed by the computer may be a program for executing the processes in chronological order described in the present specification, or the program may be a program for executing the processes in parallel or for executing the processes at necessary timing such as when the processes are invoked.

In addition, the system in the present specification denotes the entire apparatus including a plurality of apparatuses.

Note that the advantageous effects described in the present specification are illustrative only, and the advantageous effects are not limited. There may also be other advantageous effects.

Note that the embodiment of the present technique is not limited to the embodiment described above, and various changes can be made without departing from the scope of the present technique.

Note that the present technique can also be configured as follows.

(1)
A medical image processing apparatus including:
a coefficient calculation unit that calculates a correlation coefficient representing a correlation between a normal frame, the normal frame being imaged in a state in which normal light is applied to a subject, and a special frame, which is imaged in a state in which special light is applied to the subject; and
a processing unit that applies image processing to the special frame so that a part in which the correlation coefficient is high and a part in which the correlation coefficient is low are displayed differently in the special frame.

(2)
The medical image processing apparatus according to (1), further including:
a first determination unit that calculates, for each pixel or each area of the normal frame, a first determination value representing a probability that a predetermined site is imaged; and
a second determination unit that calculates, for each pixel or each area of the special frame, a second determination value representing a probability that a predetermined site is imaged, in which
the coefficient calculation unit uses the first determination value and the second determination value to calculate the correlation coefficient.

(3)
The medical image processing apparatus according to (2), in which
the first determination unit calculates the first determination value from a first gain, which is calculated from a difference between a maximum value and a minimum value of pixel values of pixels positioned around a pixel or an area to be processed in the normal frame, and a second gain, which is calculated from a degree of similarity to a color of the predetermined site.

(4)
The medical image processing apparatus according to (2) or (3), in which
the second determination unit calculates the second determination value from a third gain, which is calculated from a difference between a maximum value and a minimum value of pixel values of pixels positioned around a pixel or an area to be processed in the special frame, and a fourth gain, which is calculated from a luminance of the pixel or the area to be processed.

(5)
The medical image processing apparatus according to any one of (1) to (4), in which
the medical image processing apparatus combines the normal frame and the special frame to generate a combined frame.

(6)
The medical image processing apparatus according to (5), in which
the combined frame includes a frame in which the special frame processed by the processing unit is combined with the normal frame.

(7)
The medical image processing apparatus according to any one of (1) to (6), in which
the processing unit applies the image processing to the special frame so that the part in which the correlation coefficient is high and the part in which the correlation coefficient is low are displayed in different colors.

(8)
The medical image processing apparatus according to (7), in which
the colors are set to colors that change in stages according to the correlation coefficient.

(9)
The medical image processing apparatus according to any one of (1) to (6), in which
the processing unit applies the image processing to the special frame so that the part in which the correlation coefficient is high and the part in which the correlation coefficient is low are displayed in different brightness.

(10)
The medical image processing apparatus according to any one of (1) to (6), in which
the processing unit applies the image processing to the special frame so that one of the part in which the correlation coefficient is high and the part in which the correlation coefficient is low is flashed and displayed.

(11)
The medical image processing apparatus according to any one of (1) to (10), in which
the predetermined site includes a blood vessel,
the correlation coefficient includes a coefficient indicating that the correlation is strong between a part that is a blood vessel in the normal frame and a part that is a blood vessel in the special frame, the correlation coefficient includes a coefficient indicating that the correlation is weak between a part that is not a blood vessel in the normal frame and a part that is a blood vessel in the special frame, and
the processing unit processes the special frame so that the part with the strong correlation and the part with the weak correlation are displayed differently.

(12)
The medical image processing apparatus according to (11), in which
the correlation coefficient includes a coefficient that depends on a depth of the blood vessel, a thickness of the blood vessel, and characterization of tissue up to the blood vessel.

(13)
A medical image processing method including the steps of:
calculating a correlation coefficient representing a correlation between a normal frame, which is imaged in a state in which normal light is applied to a subject, and a special frame, which is imaged in a state in which special light is applied to the subject; and
applying image processing to the special frame so that a part in which the correlation coefficient is high and a part in which the correlation coefficient is low are displayed differently is the special frame.

(14)
A computer-readable program for causing a computer to execute a process including the steps of:
calculating a correlation coefficient representing a correlation between a normal frame, which is imaged in a state in which normal light is applied to a subject, and a special frame, which is imaged in a state in which special light is applied to the subject; and
applying image processing to the special frame so that a part in which the correlation coefficient is high and a part in which the correlation coefficient is low are displayed differently in the special frame.

REFERENCE SIGNS LIST

110 Endoscope apparatus, 111 Light source unit, 112 Imaging unit, 113 Development unit, 114 Image processing unit, 115 Display unit, 121 Switch unit, 122 Motion vector detection unit, 123 Correction amount estimation unit, 124 Frame memory, 125 Motion correction unit, 126 Superimposition processing unit, 131, 132 Frame memory, 133 Frame selection unit, 134 Block matching unit, 135 Vector correction unit, 401, 402 Determination value calculation unit, 403 Correlation coefficient calculation unit, 404 Combined frame generation unit

The invention claimed is:

1. A medical image processing apparatus comprising: a coefficient calculation unit that calculates a correlation coefficient representing a correlation between a normal frame, the normal frame being imaged in a state in which normal light is applied to a subject, and a special frame, which is imaged in a state in which special light is applied to the subject; and a processing unit that applies image processing to the special frame so that a part in which the correlation coefficient is high and a part in which the correlation coefficient is low are displayed differently in the special frame,
a first determination unit that calculates, for each pixel or each area of the normal frame, a first determination value representing a probability that a predetermined site is imaged; and
a second determination unit that calculates, for each pixel or each area of the special frame, a second determination value representing a probability that a predetermined site is imaged,
wherein the coefficient calculation unit uses the first determination value and the second determination value to calculate the correlation coefficient.

2. The medical image processing apparatus according to claim 1, wherein
the first determination unit calculates the first determination value from a first gain, which is calculated from a difference between a maximum value and a minimum value of pixel values of pixels positioned around a pixel or an area to be processed in the normal frame, and a second gain, which is calculated from a degree of similarity to a color of the predetermined site.

3. The medical image processing apparatus according to claim 1, wherein
the second determination unit calculates the second determination value from a third gain, which is calculated from a difference between a maximum value and a minimum value of pixel values of pixels positioned around a pixel or an area to be processed in the special frame, and a fourth gain, which is calculated from a luminance of the pixel or the area to be processed.

4. The medical image processing apparatus according to claim 1, wherein
the medical image processing apparatus combines the normal frame and the special frame to generate a combined frame.

5. The medical image processing apparatus according to claim 4, wherein
the combined frame includes a frame in which the special frame processed by the processing unit is combined with the normal frame.

6. The medical image processing apparatus according to claim 1, wherein
the processing unit applies the image processing to the special frame so that the part in which the correlation coefficient is high and the part in which the correlation coefficient is low are displayed in different colors.

7. The medical image processing apparatus according to claim 6, wherein
the colors are set to colors that change in stages according to the correlation coefficient.

8. The medical image processing apparatus according to claim 1, wherein
the processing unit applies the image processing to the special frame so that the part in which the correlation coefficient is high and the part in which the correlation coefficient is low are displayed in different brightness.

9. The medical image processing apparatus according to claim 1, wherein
the processing unit applies the image processing to the special frame so that one of the part in which the correlation coefficient is high and the part in which the correlation coefficient is low is flashed and displayed.

10. A medical image processing apparatus comprising:
a coefficient calculation unit that calculates a correlation coefficient representing a correlation between a normal frame, the normal frame being imaged in a state in which normal light is applied to a subject, and a special frame, which is imaged in a state in which special light is applied to the subject and
a processing unit that applies image processing to the special frame so that a part in which the correlation coefficient is high and a part in which the correlation coefficient is low are displayed differently in the special frame, wherein
the predetermined site includes a blood vessel,
the correlation coefficient includes a coefficient indicating that the correlation is strong between a part that is a blood vessel in the normal frame and a part that is a blood vessel in the special frame, the correlation coefficient includes a coefficient indicating that the correlation is weak between a part that is not a blood vessel in the normal frame and a part that is a blood vessel in the special frame, and
the processing unit processes the special frame so that the part with the strong correlation and the part with the weak correlation are displayed differently.

11. The medical image processing apparatus according to claim 10, wherein
the correlation coefficient includes a coefficient that depends on a depth of the blood vessel, a thickness of the blood vessel, and characterization of tissue up to the blood vessel.

12. A medical image processing method comprising the steps of:
calculating a correlation coefficient representing a correlation between a normal frame, which is imaged in a state in which normal light is applied to a subject, and a special frame, which is imaged in a state in which special light is applied to the subject;
applying image processing to the special frame so that a part in which the correlation coefficient is high and a part in which the correlation coefficient is low are displayed differently in the special frame,
calculating, for each pixel or each area of the normal frame, a first determination value representing a probability that a predetermined site is imaged; and
calculating, for each pixel or each area of the special frame, a second determination value representing a probability that a predetermined site is imaged,
wherein the correlation coefficient is calculated using the first determination value and the second determination value.

13. A computer-readable program for causing a computer to execute a process comprising the steps of:
calculating a correlation coefficient representing a correlation between a normal frame, which is imaged in a state in which normal light is applied to a subject, and a special frame, which is imaged in a state in which special light is applied to the subject; and
applying image processing to the special frame so that a part in which the correlation coefficient is high and a part in which the correlation coefficient is low are displayed differently in the special frame,
calculating, for each pixel or each area of the normal frame, a first determination value representing a probability that a predetermined site is imaged; and
calculating, for each pixel or each area of the special frame, a second determination value representing a probability that a predetermined site is imaged,
wherein the correlation coefficient is calculated using the first determination value and the second determination value.

* * * * *